(12) United States Patent
Norrby

(10) Patent No.: US 8,087,782 B2
(45) Date of Patent: Jan. 3, 2012

(54) DEVICES AND METHODS OF SELECTING INTRAOCULAR LENSES

(75) Inventor: Sverker Norrby, Leek (NL)

(73) Assignee: AMO Groningen B.V., Santa Ana, CA (US)

( * ) Notice: Subject to any disclaimer, the term of this patent is extended or adjusted under 35 U.S.C. 154(b) by 677 days.

(21) Appl. No.: 11/270,991

(22) Filed: Nov. 11, 2005

(65) Prior Publication Data

US 2007/0260157 A1    Nov. 8, 2007

Related U.S. Application Data

(60) Provisional application No. 60/627,430, filed on Nov. 12, 2004.

(30) Foreign Application Priority Data

Nov. 12, 2004 (SE) ...................... 0402769

(51) Int. Cl.
*A61B 3/00* (2006.01)
(52) U.S. Cl. ...................................... 351/246
(58) Field of Classification Search ................. 351/246, 351/247, 161, 177; 623/6.23–6.27, 905, 623/907, 6.11, 6.56; 606/107; 264/1.7
See application file for complete search history.

(56) References Cited

U.S. PATENT DOCUMENTS

| | | | |
|---|---|---|---|
| 4,710,193 A * | 12/1987 | Volk | 623/6.23 |
| 5,050,981 A | 9/1991 | Roffman | |
| 5,760,871 A | 6/1998 | Kosoburd et al. | |
| 5,777,719 A | 7/1998 | Williams et al. | |
| 5,968,095 A | 10/1999 | Norrby | |
| 6,050,687 A | 4/2000 | Bille et al. | |
| 6,095,651 A | 8/2000 | Williams et al. | |
| 6,224,211 B1 | 5/2001 | Gordon | |
| 6,338,559 B1 | 1/2002 | Williams et al. | |
| 6,413,276 B1 | 7/2002 | Werblin | |
| 6,499,843 B1 | 12/2002 | Cox et al. | |
| 6,663,240 B2 | 12/2003 | Patel | |
| 6,695,880 B1 | 2/2004 | Roffman et al. | |
| 6,786,603 B2 | 9/2004 | Altmann | |
| 6,808,265 B2 | 10/2004 | Cox | |
| 6,808,266 B2 | 10/2004 | Youssefi | |
| 6,817,714 B2 | 11/2004 | Altmann | |
| 6,830,712 B1 | 12/2004 | Roffman et al. | |
| 6,905,641 B2 | 6/2005 | Platt et al. | |

(Continued)

FOREIGN PATENT DOCUMENTS

JP    09196820 A2    7/1997

(Continued)

OTHER PUBLICATIONS

Hill, MD, FACS, Making IOL power calculation more powerful, *EyeWorld*, Mar. 17-22, 2006. Retrieved from World Wide Web on Jan. 6, 2006.

(Continued)

*Primary Examiner* — Ricky Mack
*Assistant Examiner* — Mahidere Sahle

(57) ABSTRACT

The invention relates to devices and methods for selecting IOLs for implantation and eye models useful with the methods. One method comprises the steps of determining the axial eye length, the pupil size at a desired light level; the desired postoperative refraction; determining an aspheric representation of the corneal curvature and determining the location of the plane of fixation of the IOL following implantation.

16 Claims, 11 Drawing Sheets

U.S. PATENT DOCUMENTS

| | | | |
|---|---|---|---|
| 2002/0105617 A1* | 8/2002 | Norrby et al. | 351/177 |
| 2003/0053025 A1* | 3/2003 | Turner et al. | 351/205 |
| 2003/0128336 A1 | 7/2003 | Jethmalani et al. | |
| 2004/0057014 A1 | 3/2004 | Altmann | |
| 2004/0085515 A1 | 5/2004 | Roffman et al. | |
| 2004/0088050 A1 | 5/2004 | Norrby et al. | |
| 2004/0100619 A1 | 5/2004 | Olivier et al. | |
| 2004/0119174 A1 | 6/2004 | Hofmann et al. | |
| 2004/0156013 A1 | 8/2004 | Lindacher et al. | |
| 2004/0246440 A1 | 12/2004 | Andino et al. | |
| 2005/0007551 A1 | 1/2005 | Wakil et al. | |
| 2005/0056953 A1 | 3/2005 | Hofmann et al. | |
| 2005/0074616 A1 | 4/2005 | Harchanko et al. | |
| 2005/0099597 A1* | 5/2005 | Sandstedt et al. | 351/168 |
| 2005/0104240 A1 | 5/2005 | Jethmalani et al. | |
| 2005/0105048 A1 | 5/2005 | Warden et al. | |
| 2005/0122472 A1 | 6/2005 | Fisher et al. | |
| 2005/0195361 A1 | 9/2005 | Jethmalani et al. | |
| 2005/0200809 A1 | 9/2005 | Dreher et al. | |
| 2005/0270491 A1* | 12/2005 | Dai et al. | 351/246 |
| 2006/0238702 A1* | 10/2006 | Glick et al. | 351/160 R |
| 2006/0274268 A1* | 12/2006 | Andino et al. | 351/212 |
| 2009/0036980 A1* | 2/2009 | Norrby et al. | 623/5.11 |

FOREIGN PATENT DOCUMENTS

| | | |
|---|---|---|
| WO | 02/088830 A1 | 11/2002 |
| WO | 03/022137 A2 | 3/2003 |
| WO | 03/057022 A1 | 7/2003 |
| WO | 03/096927 A2 | 11/2003 |
| WO | 2004/028356 A1 | 4/2004 |
| WO | 2004/039554 A2 | 5/2004 |
| WO | 2004/060643 A1 | 7/2004 |
| WO | 2004/072709 A1 | 8/2004 |
| WO | 2004/096014 A2 | 11/2004 |

OTHER PUBLICATIONS

Norrby, Ph.D. et al. Comparison of 2 A-scans. *J Cataract Refractive Surgery*. vol. 29, Jan. 2003, pp. 95-99.

Norrby, Ph.D. et al. Reduction of trend errors in power calculation by linear transformation of measured axial lengths. *J Cataract Refractive Surgery*. vol. 29, Jan. 2003, pp. 100-105.

Norrby, Ph.D. et al. Clinical application of the lens haptic plane concept with transformed axial lengths, *J. Cataract Refractive Surgery*, vol. 31, Jul. 2005, pp. 1338-1344.

Preussner, M.D., Ph.D., et al. Predicting postoperative intraocular lens position and refraction. *J. Cataract Refractive Surgery*. vol. 30, Oct. 2004, pp. 2077-2083.

Norrby, "The Dubbelman eye model analysed by ray tracing through aspheric surfaces", The college of Optometrists: 2005 25: 153-161.

* cited by examiner

FIG. 6

| | A | B | C | D | E | F | G | H | I | J |
|---|---|---|---|---|---|---|---|---|---|---|
| 1 | Ray tracing example | | CALCULATION PARAMETERS | spectacle-a | spectacle-b | cornea-a | cornea-p | lens-a | lens-p | receptors |
| 2 | | | thickness on axis | 5986.00 | 2.00 | 12.00 | 0.50 | 4.40 | 1.13 | 17.97 |
| 3 | INPUT | | refractive index | 1.000 | 1.500 | 1.000 | 1.376 | 1.336 | 1.458 | 1.336 |
| 4 | target distance | 6000 | radius at apex | 83.86 | 83.33 | 7.70 | 6.80 | 12.154 | -12.154 | -23.00 |
| 5 | axial length | 23.77 | conic constant | 1.00 | 1.00 | 0.82 | 0.66 | -5.00 | -5.00 | 1.00 |
| 6 | transf. const. | 0.23 | x at vertex | -14.00 | -12.00 | 0.00 | 0.50 | 4.90 | 6.03 | 24.00 |
| 7 | pupil | 5.0 | x intersect | -13.98 | -11.98 | 0.20 | 0.72 | 4.99 | 5.95 | 24.00 |
| 8 | relative ray height | 0.707 | y intersect | 1.77 | 1.75 | 1.76 | 1.72 | 1.48 | 1.42 | 0.0000 |
| 9 | Δx | 0.0001 | x between intersects | 5986 | 2.00 | 12.18 | 0.52 | 4.27 | 0.96 | 18.05 |
| 10 | | | x ray from apex to intersect | 0.018633 | 0.018463 | 0.202767 | 0.221109 | 0.088474 | -0.081569 | 0.000000 |
| 11 | | | x surface from apex to intersect | 0.018633 | 0.018463 | 0.202767 | 0.221109 | 0.088474 | -0.081569 | 0.000000 |
| 12 | OUTPUT | | x difference ray-surface | 0.000000 | 0.000000 | 0.000000 | 0.000000 | 0.000000 | 0.000000 | 0.000000 |
| 13 | spectacle refraction | 0.01 | x+Δx | 0.018635 | 0.018465 | 0.202790 | 0.221135 | 0.088486 | -0.081580 | 0.000000 |
| 14 | composed of: | | x-Δx | 0.018631 | 0.018461 | 0.202744 | 0.221083 | 0.088463 | -0.081557 | 2.73E+07 |
| 15 | front power | 5.96 | differential | 47.43 | 47.50 | 4.29 | 3.86 | 8.51 | -8.85 | -0.0785 |
| 16 | back power | -6.00 | α between in ray and axis | 0.0003 | -0.0068 | 0.0003 | -0.0631 | -0.0573 | -0.0623 | 1.5708 |
| 17 | thickness power | 0.05 | β between tangent and axis | 1.5497 | 1.5497 | 1.3416 | 1.3172 | 1.4539 | 1.6833 | -0.0785 |
| 18 | | | γ between in ray and normal | 0.0214 | 0.0142 | 0.2295 | 0.1905 | 0.0596 | 0.1749 | |
| 19 | | | δ between out ray and normal | 0.0142 | 0.0213 | 0.1661 | 0.1963 | 0.0546 | 0.1910 | |
| 20 | | | ε between out ray and axis | -0.0068 | 0.0003 | -0.0631 | -0.0573 | -0.0623 | -0.0785 | |

FIG. 7

DEVICES AND METHODS OF SELECTING INTRAOCULAR LENSES

RELATED APPLICATIONS

The application claims priority to U.S. provisional patent application No. 60/627,430, filed Nov. 12, 2004, and to SE application no. 0402769-4, filed Nov. 12, 2004, now abandoned.

BACKGROUND OF THE INVENTION

1. Field of the Invention

The present invention relates generally to devices and methods for selecting an intraocular lens and more specifically to devices and methods of finding suitable powers and/or locations of intraocular lenses to be implanted into an eye in order to obtain a predetermined refractive outcome, taking into account such parameters as the asphericity of the cornea and/or the intraocular lens.

2. Description of the Related Art

U.S. Pat. No. 5,968,095, herein incorporated by reference, refers to a method of preoperatively selecting the power of an intraocular lens (IOL) to be implanted into an eye having a lens haptic plane. The method involves selecting eye parameters to construct an eye model for finding a correct representation of the intraocular lens as axially positioned in the eye following surgical implantation. However, this method is not designed to be applicable when any of the optical surfaces is aspheric. In particular this method is not applicable when using aspheric lenses designed to reduce or eliminate the spherical aberration of the cornea. Other commonly applied methods to determine IOL power, such as the widely used SRK/T formula, and other widely applied methods such as the Hoffer Q and Holladay 1 and Holladay 2 formulas, suffer the same shortcoming in being based on thin lens vergence calculations and/or spherical lens surfaces. Paul-Rolf Preussner et al. disclose an alternative method of predicting outcome of choice of IOL model and power in J Cataract Refract Surg, 2004, Vol. 30, pp. 2077-2083, which is herein incorporated by reference.

As aspheric IOLs capable of correcting spherical aberrations now are becoming available on the market (e.g., Tecnis® brand of IOL, available from AMO Inc., Santa Ana, Calif.), there is a demand to obtain reliable methods to select aspheric IOL powers in order to achieve the desired patient outcome in terms of spectacle correction and/or image quality.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following figures, with like numerals indicating like parts:

FIG. 6 is printout of the formulas programmed into each cell of an Excel spreadsheet used to provide the ray tracing program in accordance with embodiments of the present invention.

FIG. 7 is illustrates the numerical result of the calculation in each cell of an Excel spreadsheet used to provide the ray tracing program in accordance with embodiments of the present invention.

DETAILED DESCRIPTION OF THE DRAWINGS

Figure 1:
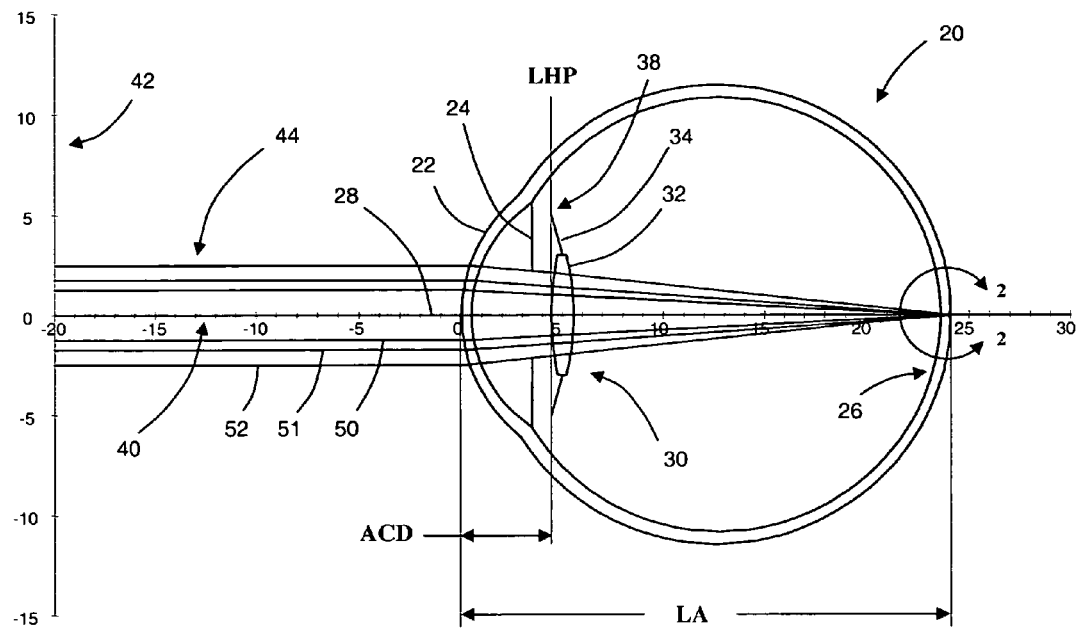
FIG. 1 is a graphical representation of elements of an eye model used in various embodiments of the present invention.

The present invention is directed to reliable methods and devices for selecting spherical and aspheric intraocular lenses (IOLs) that provide a predetermined refractive outcome for patients in need of cataract or refractive surgery. Embodiments of the invention may be understood by reference FIG. 1, which is a graphical representation of a model of an eye 20 comprising a cornea 22, an iris 24, a retina 26, and an optical axis 28. An IOL 30 is disposed within the eye 20, the IOL 30 comprising an optic 32 and one or more haptics 34 having distal ends 38. In general, the eye model may consist of the dimensional parameters illustrated by the geometry shown in FIG. 1, for example, the axial length of the eye (AL) and the anterior chamber depth (ACD). Other dimensional parameters that may be included in the eye model that are not shown in FIG. 1 include, but are not limited to, the corneal radius (CR), the corneal power (K), and crystalline lens thickness (LT). The eye model may also include various other parameters such as, for example, the refractive indices of the various portions of the eye 20 and/or the IOL 30. In certain embodiments, the distal ends 38 of the haptics 34 are disposed within a plane defined a lens haptic plane (LHP). In other embodiments, other information of the IOL 30 may be included in the eye model such as, for example, an effective principal plane of the optic 32 or other information regarding the optic 32 useful in determining the performance optic 32 and/or the location of the optic 32 within the eye 20.

The graphical representation of the eye model illustrated in FIG. 1 also has a coordinate system containing a horizontal axis 40 and a vertical axis 42, which are labelled in units of millimeters. The graphical representation illustrated in FIG. 1 also shows a plurality of rays 44 entering cornea 22 and the IOL 30 of the eye model. The plurality of rays 44 comprises a paraxial ray 50 that is disposed near the optical axis 28 and a marginal ray 52 that is disposed near edge of the opening formed by the iris 24. The plurality of rays 44 additionally comprises an averaged ray 51 disposed between the paraxial ray 50 and the marginal ray 52, for example, at a height at the pupil that is $1/\sqrt{2}$ or ½ times the height of the entrance pupil height. In some embodiments, the eye model additionally contains information regarding an object or source represented by the plurality of rays 44 entering the eye 20, for example, the distance of the source or object from the eye 20 and/or the extent of the source or object in units of length or are length.

Figure 2A:
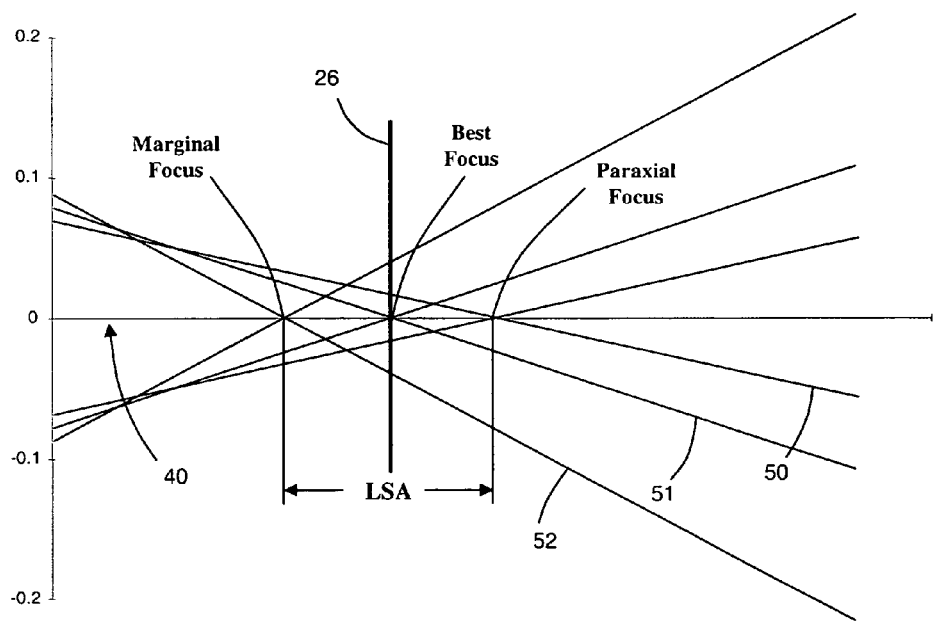
FIG. 2a and 2b are magnified views of the corneal region of the graphical representation shown in FIG. 1
Figure 2B:
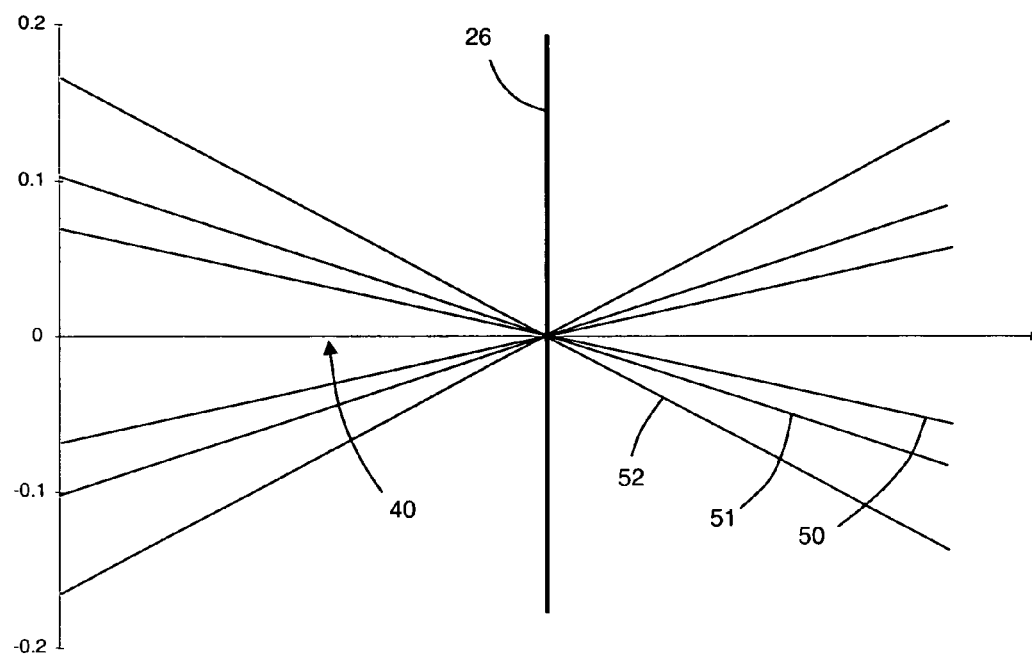

Referring to FIG. 2a, which is a magnified view of the region around retina 28, the rays 50-52 may come to focus at different points along the optical axis 28, which are labelled in the figure as marginal focus, best focus, and paraxial focus. As illustrated in the figure, the distance between the marginal focus and the marginal focus may be used to define a longitudinal spherical aberration (LSA). Such a result may be produced, for example, when the surfaces of the IOL 30 are spherical. Alternatively, one or more of the surfaces of the IOL 30 may comprise an aspheric profile that is configured to reduce or eliminate spherical aberrations produced either by an IOL made of spherical surfaces or by at least portions of the eye 20 (e.g., the cornea 22). In such embodiments, as illustrated in FIG. 2b, the rays 50-52 focus to a common or substantially common point along the optical axis 28.

Embodiments of the invention may be used in conjunction with an eye model such as that illustrated in FIG. 1 to select or determine a characteristic of an IOL to be implanted into the eye of a subject or a class of subjects, for examples subjects of a particular age group or condition (e.g., a class of subjects who have had a LASIK or similar procedure). In certain embodiments, measurements from a subjects eye (e.g., AL, ACD, CR, LT) may be used in conjunction with statistical data and/or an analytical tool (e.g., a ray trace program or algorithm) to determine the characteristic of the IOL. The characteristic of the IOL resulting from embodiments of the invention may include the thickness of the IOL, the power of the IOL, the asphericity of the IOL, and/or the location of the IOL within the eye of the subject or subjects.

Figure 3:
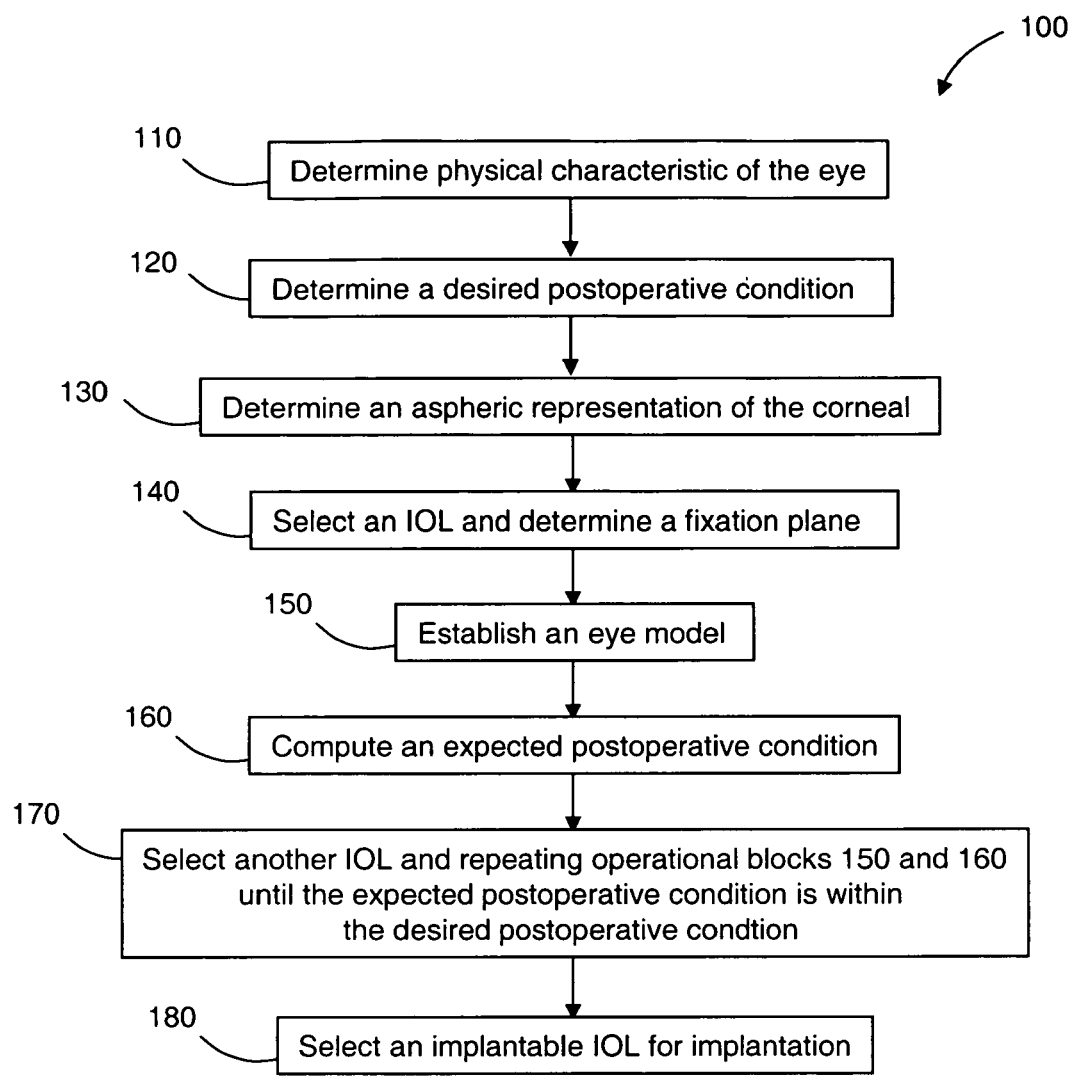
FIG. 3 is a flow chart showing a method of selecting an IOL according to one embodiment of the invention.

Referring to FIG. 3, in certain embodiments, a method 100 of selecting an IOL comprises one or more of the following operational blocks 110-180. The method 100 comprises an operational block 110, which comprises determining physical characteristic of the eye such as an axial eye length or a pupil size at a desired light level. The method 100 further comprises an operational block 120, which comprises determining a desired postoperative condition such as a postoperative refraction and/or spherical aberration. The method 100 further comprises an operational block 130, which comprises determining an aspheric representation of the corneal curvature or curvatures. The method 100 also comprises an operational block 140, which comprises selecting an IOL with one or more predetermined characteristics (e.g., with a predetermined power or asphericity) and determining the location of a plane of fixation of the IOL following implantation (e.g., the lens haptic plane or LHP). The method 100 additionally comprises an operational block 150, which comprises employing the results of operational blocks 110-140 to establish an eye model. The method 100 also comprises an operational block 160, which comprises computing, by means of an analytical tool (e.g., a ray tracing routine) with said eye model, an expected postoperative condition such as an expected postoperative refraction and/or spherical aberration. The method 100 further comprises an operational block 170, which comprises, in the case the expected postoperative condition is not within the desired postoperative condition, selecting another IOL with different power and/or asphericity and repeating operational blocks 150 and 160 until the expected postoperative condition is within the desired postoperative condition. The method 100 may also comprise an operational block 180, which comprises selecting, for implantation, an implantable IOL of the nearest power and asphericity available or designing an implantable IOL that results in the desired postoperative refraction and spherical aberration.

The method 100 may also include transforming the measured axial length to a human population average scale by adding to the value a transformation constant. The axial length measured by ultrasound is not the same as the optical axial length, and as the axial length measured by one piece of equipment may differ from that measured by another one, there is a benefit to obtaining instrument independent measurements. Measurement of axial eye length for an individual patient may be obtained by ultrasound A-scan or the newer partial coherence inter-ferometry (PCI) principle, available with the Zeiss IOLMaster. Regardless of the instrument and/or method used, the axial eye length may first be transformed to a human population average (HPA) scale. In certain embodiments, an underlying assumption for the HPA scale is that the mean axial length is about constant in any large group of adults. Transformation is discussed in more detail by Norrby et al. (J Cataract Refract Surg 2003; 29:100-105) and the HPA scale is introduced by Norrby et al. (J Cataract Refract Surg 2005; 31:1338-1344), both of which are herein incorporated by reference. Transformation amounts to the addition of a correction constant to the measured axial eye length. The correction constant is generally regarded as instrument specific, for example, as described in Norrby et al. (J Cataract Refract Surg 2005; 31:1338-1344). A general outline of a routine to obtain a common scale for axial lengths may include the following steps. First the postoperative anterior chamber depth consistent with axial length, corneal radius, postoperative refraction and IOL power implanted are calculated by thick lens ray tracing for a number of individual cases. The mean of the calculated anterior chamber depths may be calculated and compared with a previous study with the same lens (e.g., Pharmacia CeeOn® 809C brand of IOL published in Koranyi et al.: J Cataract Refract Surg, 2002; 28:243-247, herein incorporated by reference). The measured axial lengths may then be transformed by addition of a constant value, and the mean anterior chamber depth was calculated anew. This process may be iterated until the calculated mean anterior chamber depth coincided with that of the other.

The pupil size may be measured preoperatively at the desired light level, e.g. mesopic light (dusk). The pupil size at dusk is about 4 mm, but variations between at least about 2 mm to 6 mm or more can occur.

The aspheric representation of the anterior corneal is typically derived from corneal topography, most commonly based on the so-called Placido disk principle. Resulting height maps can be used to fit an aspherical description of the surface by a least squares optimization. Slit based methods such as implemented on the Orbscan® brand of topography systems (Bausch & Lomb) may be used for the same purpose (Holladay et al. J Refract Surg 2002; 18:683-691). The Orbscan® can also be used to obtain an aspherical description of the posterior corneal surface in the same manner. Instruments based on the Scheimpflug principle, such as Nidek EAS-100, may also be used to obtain anterior and posterior curvatures of the corneal surfaces. By rotating the slit and taking multiple pictures the topography of both surfaces can be obtained. The newly presented Oculus Pentacam eye scanner, which is also based on the Scheimpflug principle, achieves this within a couple of arc seconds, and is suitable for use with the method 100.

Independent of the measurement system used, the topography for the purpose of the method 100 is conveniently described as a conicoid surface of revolution, characterized by the aspheric constant k value (conic constant), optionally extended with additional polynomial terms. Preferably, k values are obtained for both anterior and posterior corneal surfaces, optionally in combination with additional polynomial terms.

The method 100 may be used to calculate an amount of at least one of a postoperative refraction and a postoperative spherical aberration for a lens that is implantable into the eye of a subject. Preferably the calculations are carried out using a ray tracing program or procedure, although other calculating means may also be used, such as an optics design program. One benefit of the method 100 is that it is capable of reducing the amount of computation necessary when using a ray tracing procedure and yet produces reliable information for lens power selection. Accordingly, only limited numbers of rays needs to be employed with the routine rather than the great number of rays normally traced for the purpose of optical design (several software packages are commercially available, e.g., those sold under the brand names of Zemax®, OSLO®, Code V®), which are cumbersome to employ, although they could be used for the purpose of the IOL power calculation and assessment of the resulting image quality.

In one aspect of the invention a ray entering the pupil at $1/\sqrt{2}$ of the entrance pupil height is employed. This ray is here termed the focusing ray. Alternatively a ray at the full pupil diameter (marginal ray) and a ray with close to zero ray height (paraxial ray) are traced. Focus is in this case assumed to be at the midpoint of the foci of the marginal and the paraxial rays. The distance between the foci of the marginal and the paraxial rays, the longitudinal spherical aberration (LSA), can also be used as a simple metric for image quality. The smaller LSA is the better the image quality is.

According to one embodiment of the method 100, one or more of the surfaces of an IOL such as the IOL 30 are described by the formula:

$$x = \frac{\left(\frac{1}{R}\right)y^2}{1+\sqrt{1-k\left(\frac{1}{R}\right)^2 y^2}} + a_4 y^4 + a_6 y^6 + \ldots \quad (1)$$

wherein R is the radius of curvature at the apex, k the conic constant, y the radial distance from the optical axis and x the sag in the direction of light propagation. Depending on the value of k the first term is a conic section and describes a:

| | |
|---|---|
| hyperbola | $k < 0$ |
| parabola | $k = 0$ |
| prolate ellips | $0 < k < 1$ |
| circle | $k = 1$ |
| oblate ellips | $k > 1$ |

The coefficients for the additional polynomial terms $a_4$, $a_6$, etc. can either be set to zero, in which case the surface is a conicoid of revolution, or be given positive or negative non-zero values to modify the simple conic section rotational surface. Alternatively, the method 100 may be used with other forms of the above equation or other definitions of terms such as conic constant.

A method to design intraocular lenses for the purpose of correcting average corneal spherical aberration obtained from pooled corneal data of a an elected patient group is further explained in the U.S. Pat. No. 6,609,793, herein incorporated by reference. Corneas of the normal population are in the prolate range ($0<k<1$) however, the method 100 is applicable to all types of aspheric IOLs, such as IOLs with a hyperbolic (including parabolic) or oblate (including spherical) surfaces.

According to one aspect, patients having had corneal refractive surgery to correct myopia can have a hyperbolic anterior surface ($k \leq 0$), while those having had corneal refractive surgery to correct hyperopia can have an oblate anterior surface ($k \geq 1$) (Buehren et al., Scientific poster 144, AAO 2004, New Orleans). The method 100 demonstrates satisfying capacity in obtaining careful prediction of IOL powers also for such patients, including estimating the resulting retinal image quality in terms of LSA, although surfaces deviating considerably from prolate may be required.

The method 100 may further comprise obtaining the corneal apex radius, typically both anterior and posterior corneal apex radii, from the topography, or from corneal radius measured by conventional keratometry (at about 3 mm diameter) and corrected to the value at the apex by the method described by Dubbelman et al. (Vision Res 2005; 45:117-132), herein incorporated by reference.

There are both indirect and direct methods available to preoperatively determine the location of the lens haptic plane (LHP), i.e. the distance from the anterior cornea to the LHP. Direct methods include ultrasound biomicroscopy, optical coherence tomography and Scheimpflug photography as taught in U.S. Pat. No. 5,968,095, herein incorporated by reference. Newer, commercially available equipment having the capacity to conduct such direct measurements includes the following systems, which are available from the listed companies: Artemis (Ultralink LLC), Visante OCT (Zeiss), and Pentacam (Oculus).

Alternatively, the location of the lens haptic plane may be obtained with a prediction algorithm that includes preoperatively measured parameters such as axial eye length (AL), corneal radius (CR) or, alternatively, corneal power (K), anterior chamber depth (ACD), and crystalline lens thickness (LT). Norrby et al. (J Cataract Refract Surg 2005; 31:1338-1344) have studied prediction algorithms of the general type:

$$LHP = a + b \times AL + c \times ACD + d \times LT + e \times CR + \quad (2)$$
$$f \times AL^2 + g \times ACD^2 + h \times LT^2 + i \times CR^2 +$$
$$j \times AL \times ACD + k \times AL \times LT + l \times AL \times CR +$$
$$m \times ACD \times LT + n \times ACD \times CR + o \times LT \times CR$$

One finding of the study mentioned is that AL and ACD measured with one piece of equipment can deviate systematically from that measured with another piece of equipment (Norrby et al. J Cataract Refract Surg 2003; 29:95-99; see also Koranyi et al. J Cataract Refract Surg 2002; 28:243-247, and Norrby, J Cataract Refract Surg 2001; 27:1656-1661, all of which are herein incorporated by reference). To correct measured AL and ACD the concept of a Human Population Average (HPA) scale was devised (Norrby et al. J Cataract Refract Surg 2005; 31:1338-1344). Algorithms containing LT and ACD in general were found to be unreliable when employing measurements obtained with different pieces of equipment, despite correction of ACD to the HPA scale (Norrby et al. J Cataract Refract Surg 2005; 31:1338-1344). Also the early attempts to model LHP in terms of and LT and ACD (Norrby and Koranyi, J Cataract Refract Surg 1997; 23:254-259, U.S. Pat. No. 5,968,095, both of which are herein incorporated by reference) were found unreliable. Regression formulas containing CR and AL in linear, quadratic and cross-terms, with or without the constant a, in accordance with the general formula above, gave consistent results independent of the measurement equipment used, when AL was transformed to the HPA scale. A preferred algorithm is $$LHP = 2.486 + 0.2174 \times (AL + \Delta AL) - 0.4213 \times CR \quad (3)$$

wherein AL is the measured axial eye length, $\Delta AL$ is the transformation constant (ranging from 0.2 mm to 1.0 mm depending on equipment used) and CR is the keratometric corneal radius (at about 3 mm diameter); (see also S Norrby et al. J Cataract Refract Surg 2005; 31:1338-1344). The position of the IOL 30 in the eye is determined by its vault height, i.e. the distance between the LHP and the anterior apex of the IOL 30, where the LHP coincides with the plane of contact between the IOL haptics and ocular tissue (e.g. the capsular bag). The vault height is considered to be positive if the anterior IOL apex is posterior to LHP and negative if the anterior IOL apex is anterior to LHP.

The present invention also relates to an improved eye model, which admits simple ray tracing procedures to evaluate suitable intraocular lenses for implantation and to select a lens available in terms of refractive power and/or asphericity. The eye model includes values of the axial eye length based on a measured axial eye length transformed to the human population average scale by addition of a transformation constant; the pupil size at a desired light level, an aspheric representation of the corneal curvature and a value of the lens haptic plane location (the plane of fixation of an implantable IOL following implantation). Routines of how to obtain the mentioned necessary values for the eye model from an individual are described above. Besides admitting a significant calculation simplicity, the invented eye model provides estimations that are substantially independent from what type of biometric instrumentation that are used for the eye axial length.

In certain embodiments, a method comprises determining the optical quality of an eye following the implantation of an implantable IOL. The method may be based upon using the above described eye model with an aspheric IOL and a ray tracing routine, for example, in which a marginal ray and a paraxial ray are used to calculate the longitudinal spherical aberration (LSA). If an undesired high value of LSA is obtained from the method, another lens with another power and/or asphericity is selected and the method is repeated until a lens is found that provides a predetermined optical quality, as represented by a low LSA.

Figure 4:
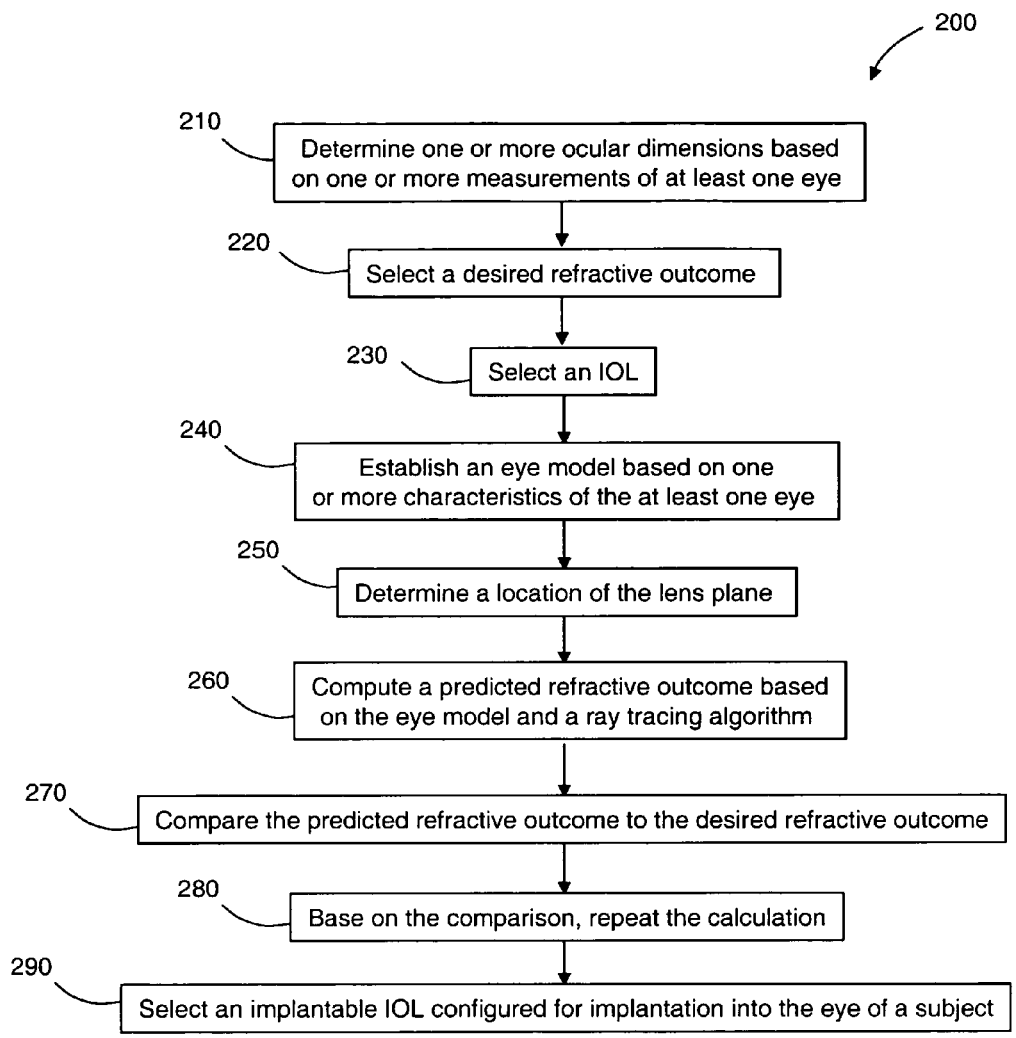
FIG. 4 is a flow chart showing a method of selecting an IOL according to another embodiment of the invention.
Figure 5:
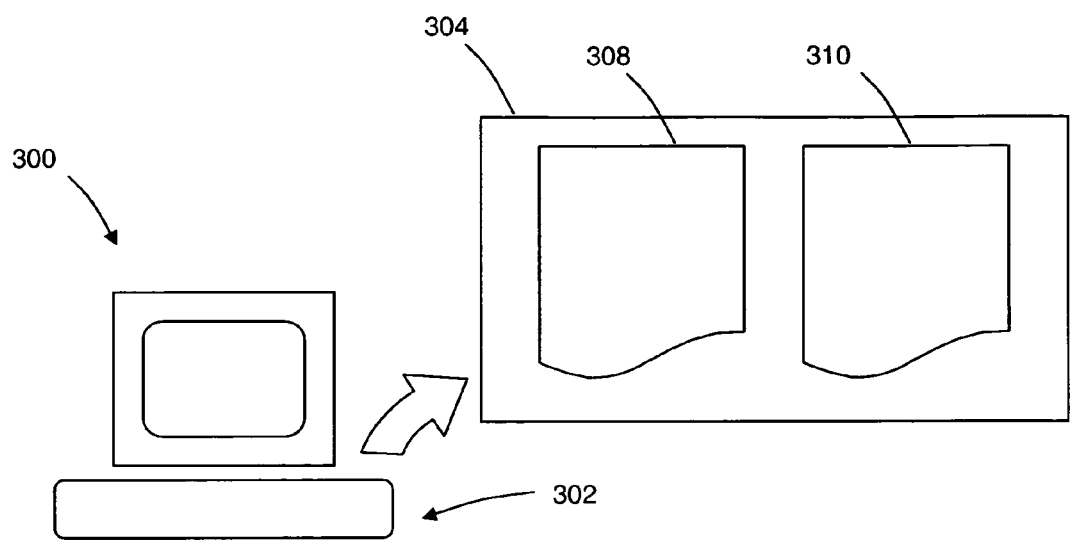
FIG. 5 is a graphical representation of the elements of computing system for selecting an IOL according to embodiments of the present invention.
Figure 8A:
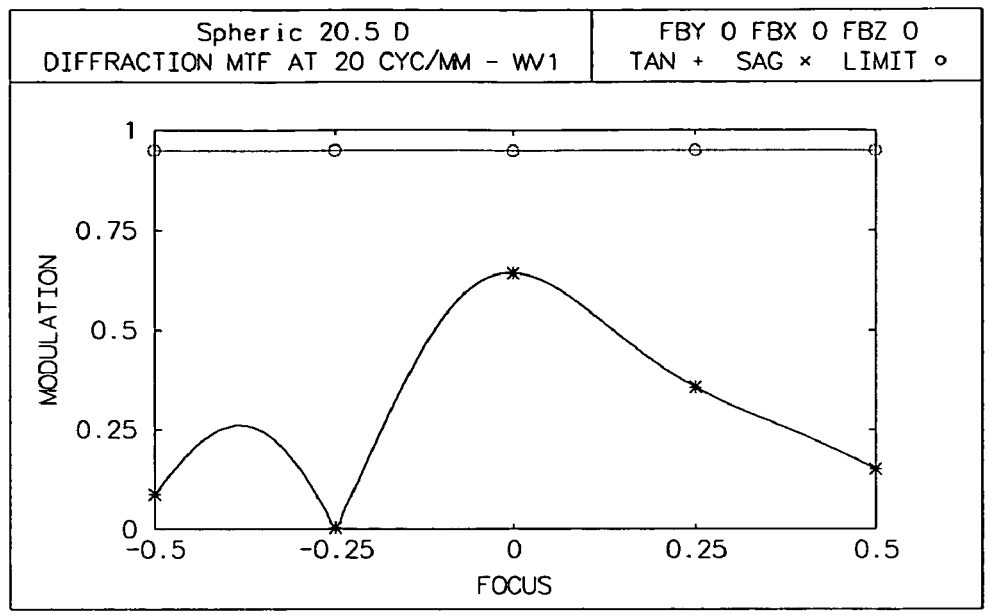
Figure 8B:
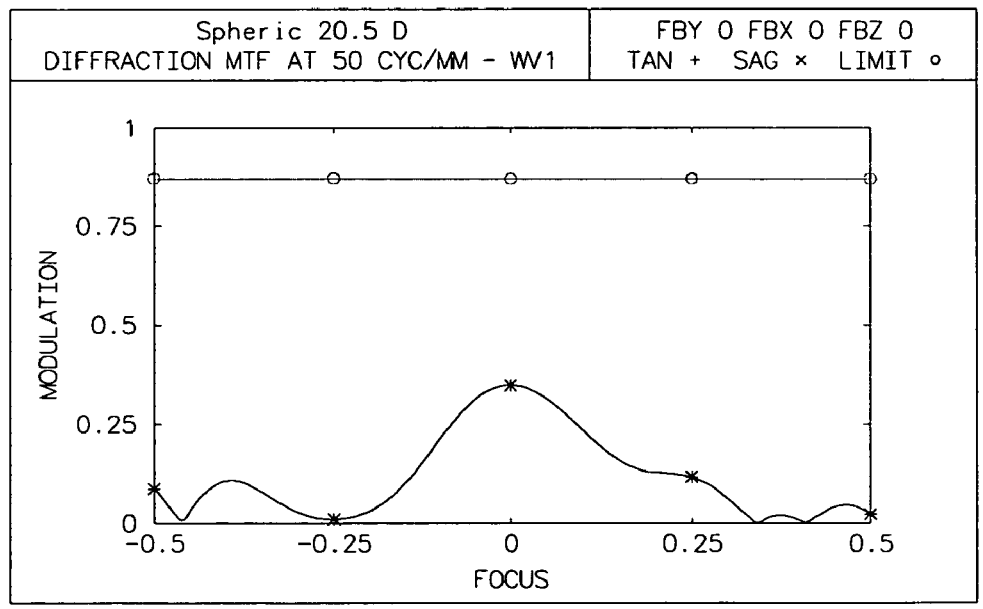
Figure 8C:
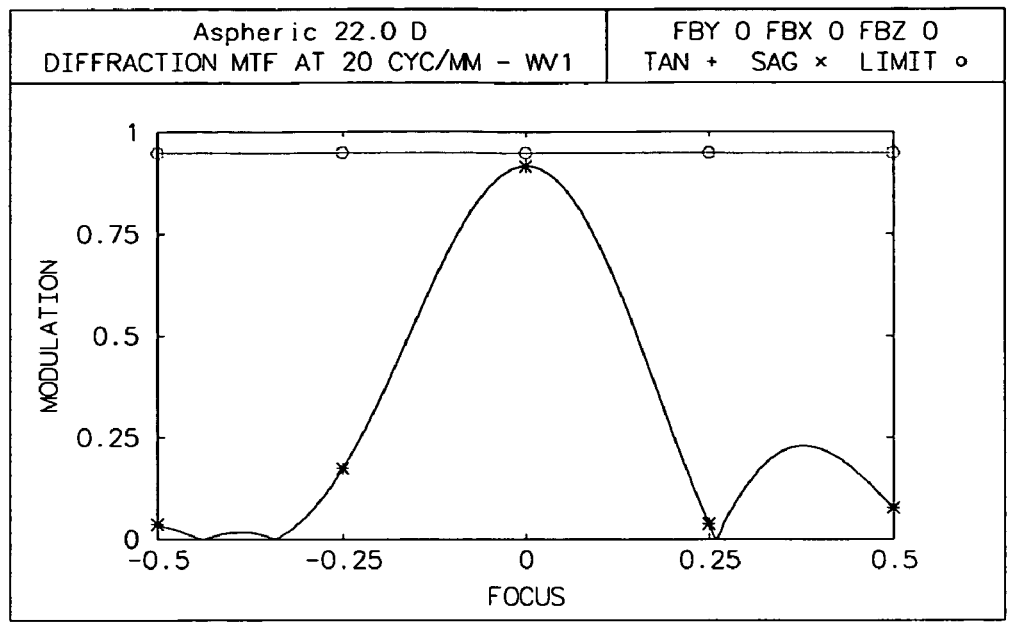
Figure 8D:
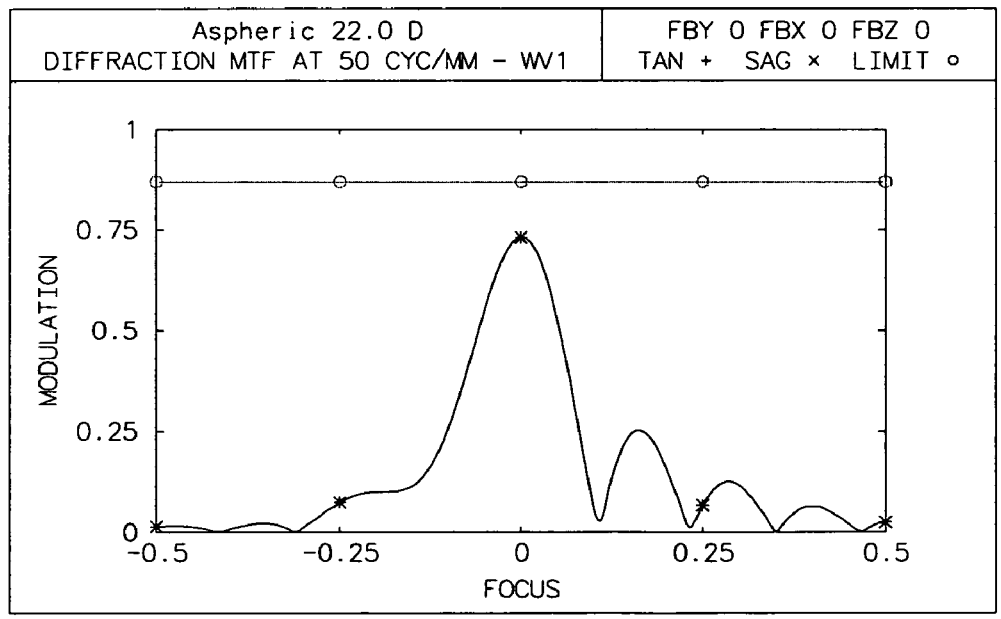
Figure 9A:
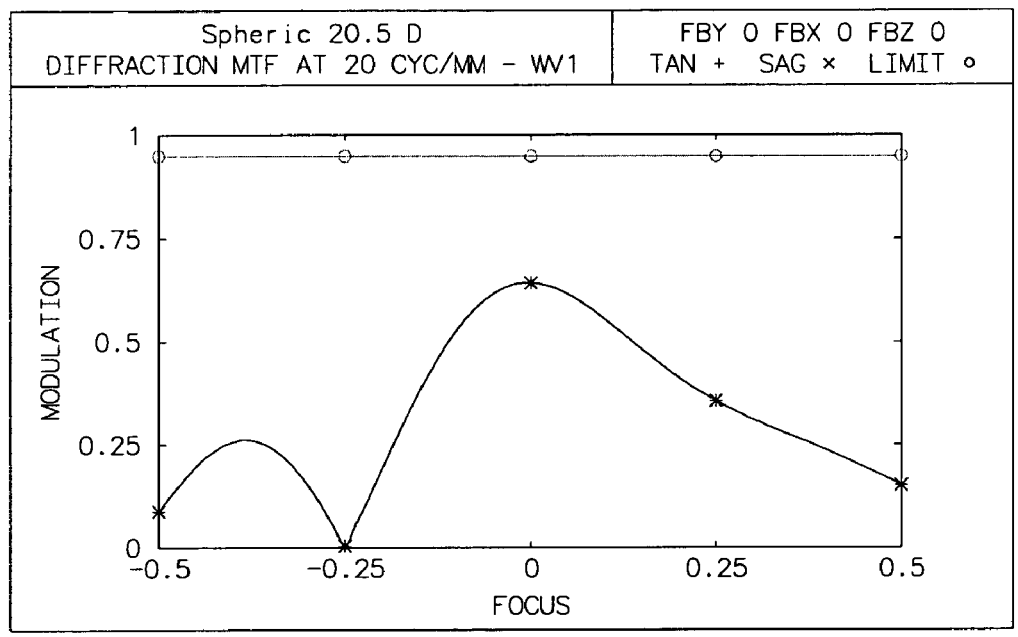
FIG. 9A-9D are through-focus MTF plots used to determine maximum MTF of an IOL.
Figure 9B:
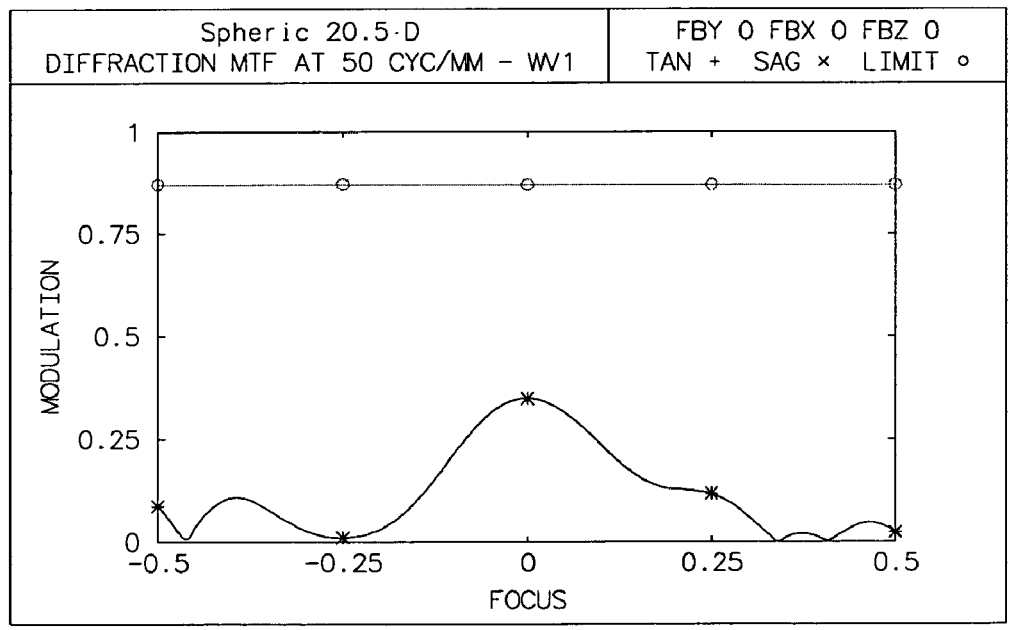
Figure 9C:
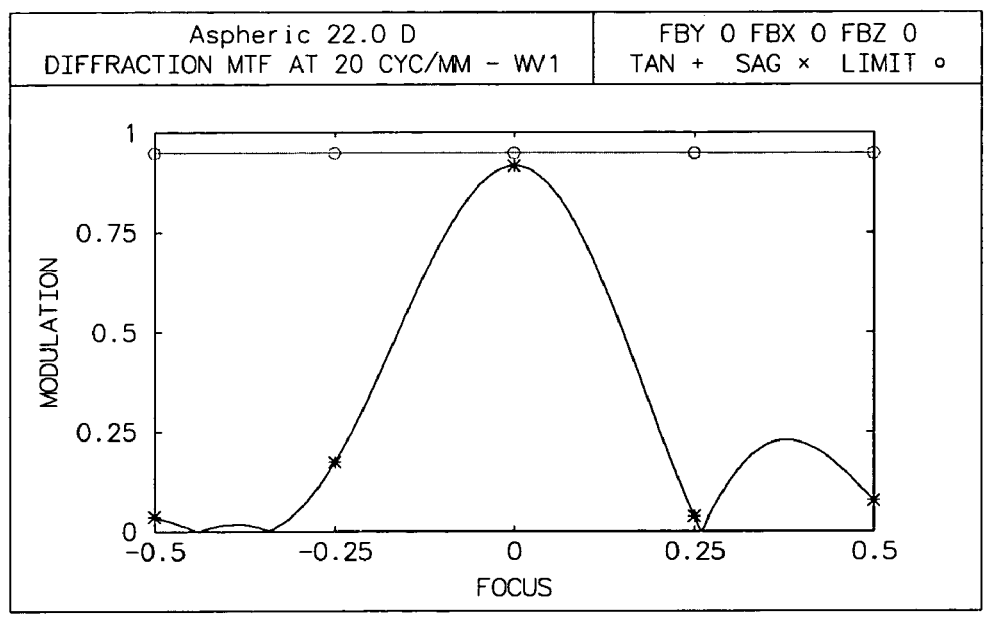
Figure 9D:
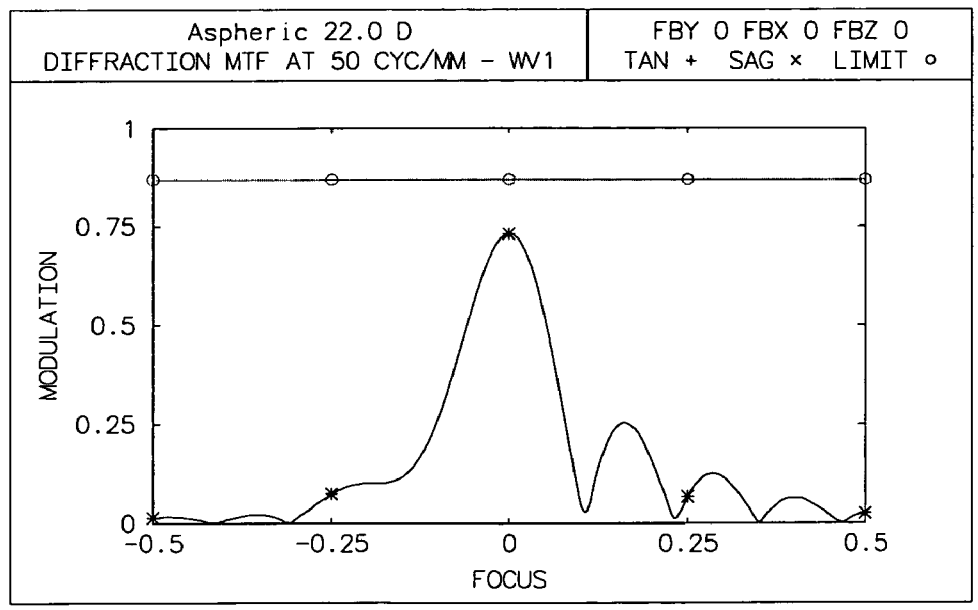

Referring to FIG. 4, in certain embodiments, a method 200 of selecting an IOL comprises one or more of the following operational blocks 210-270. Where appropriate, aspects of the method 100 discussed above herein may also be applied to embodiments of the method 200. The method 200 comprises an operational block 210, which comprises determining one or more ocular dimensions based on one or more measurements of at least one eye. The method 200 also comprises an operational block 220, which comprises selecting a desired refractive outcome. The method 200 comprises an operational block 230, which comprises selecting an IOL (e.g., the IOL 30) having at least one of a power, an aspheric profile, and a lens plane. The method 200 comprises an operational block 240, which comprises establishing an eye model based on one or more characteristics of the at least one eye. The method 200 comprises an operational block 250, which comprises determining a location of the lens plane. The method 200 comprises an operational block 260, which comprises performing a calculation to determine a predicted refractive outcome based on the eye model and a ray tracing algorithm. The method 200 comprises an operational block 270, which comprises comparing the predicted refractive outcome to the desired refractive outcome. The method 200 comprises an operational block 280, which comprises, based on the comparison, repeating the calculation with an IOL having at least one of a different power, a different aspheric profile, and a different lens plane. The method 200 comprises an operational block 290, which comprises selecting an implantable IOL configured for implantation into the eye of a subject.

Referring to operational block 210, the method 200 incorporate one or more ocular dimensions based, for example, the eye model illustrated in FIG. 1. In certain embodiments, the method 200 may incorporate data from a database of eyes or from a plurality of eyes belonging to subject belonging to a particular population such as a population of cataract patients or subjects that have received a corneal treatment for vision correction. Such data is illustrated, for instance, in U.S. Pat. Nos. 6,609,793 and 6,830,332 and U.S. Patent Application Publication 2004/088050, all herein incorporated by reference.

Referring to operational block 220, the desired refractive outcome may be, for example, providing a subject with distant vision and/or near vision. This may include providing the subject sufficient visual acuity that there is no need for external corrective spectacles or contact lenses for near and/or distant vision. Alternatively, the refractive outcome may be less stringent in terms of the degree of correction. For example the refractive outcome might to provide sufficient visual acuity such that normal vision is provided by the use of external corrective spectacles or contact lenses having a correction of less than about 3 Diopters, preferably less than 2 Diopters, and more preferably less than 1 Diopter. In some embodiments the desired refractive outcome is reduction of spherical aberrations or other higher order aberrations that would have been created by the use of, for example, and IOL having only spherical surfaces. Alternatively or additionally, the desired refractive outcome is reduction of spherical aberrations or other higher order aberrations induced by the cornea or some other part of the eye. Such criteria are discussed in U.S. Pat. No. 6,609,793.

Referring to operational block 250, the lens plane may be lens haptic plane (LHP) illustrated, for example, in FIG. 1. Alternatively, the lens plane may be some other that is appropriate for determining, for example, the power, asphericity, and/or location of an IOL in within the eye of a subject. For example, the lens plane used in the method 200 may be an effective principal plane of the optic 32. In such embodiments, a distinction may be made between lenses of various manufactures so that effect of different geometries on IOL performance may be taken into account.

Referring to operational block 260, calculation of a predicted refractive outcome is based not simply on measurements and correlation databases, such as those used in currently existing formulas such as Holladay 1 and 2, Hoffer Q, and SRK/T and a ray tracing algorithm. Rather, the current method 200 calculates a predicted refractive outcome based on a ray tracing or wavefront analysis in addition to using measurement and correlation databases. This approach has been found by the inventor to provide a more reliable way of providing a patient a lens with the correction power to provide normal vision as well as provide the possibility of correcting for higher order ocular aberrations such as spherical aberrations. The one or more ocular dimensions may include, for example, any of the dimension of any of the elements of the eye 20 illustrated in FIG. 1

In certain embodiments, a computer system 300 for selecting an IOL for placement into the eye of a subject comprises a processor 302 and a computer readable memory 304 coupled to the processor 302. The computer readable memory 304 has stored therein an array of ordered values 308 and sequences of instructions 310 which, when executed by the processor 302, cause the processor 302 to select an implantable IOL configured for implantation into the eye of a subject. The array of ordered values 308 may comprise data used or obtained from the methods 100, 200 or other methods consistent with embodiments of the invention. For example, the array of ordered values 308 may comprise one or more ocular dimensions of an eye or plurality of eyes from a database, a desired refractive outcome, parameters of an eye model based on one or more characteristics of at least one eye, and data related to an IOL or set of IOLs such as a power, an aspheric profile, and/or a lens plane. The sequence of instructions 310 may include one or more steps of the methods 100, 200 or other methods consistent with embodiments of the invention. In some embodiments, the sequence of instructions 310 includes determining a location of the lens plane of an IOL, performing one or more calculations to determine a predicted refractive outcome based on an eye model and a ray tracing algorithm, comparing a predicted refractive outcome to a desired refractive outcome, and based on the comparison, repeating the calculation with an IOL having at least one of a different power, a different aspheric profile, and a different lens plane.

The computer system 300 may be a general purpose desktop or laptop computer or may comprise hardware specifically configured performing the task of selecting an IOL for placement into the eye of a subject. In some embodiments, the computer system 300 is configured to be electronically coupled to another device such as a phacoemulsification console or one or more instruments for obtaining measurements of an eye or a plurality of eyes. In other embodiments, the computer system 300 is a handheld device that may be adapted to be electronically coupled to one of the devices just listed.

A number of examples will now be presented demonstrating how methods and devices according to embodiments of the invention may be used to determine a suitable lens for a patient in terms refractive power and/or reduced aberrations. These examples also demonstrate that these methods can be used to estimate the visual quality of the patient in terms of the longitudinal spherical aberration (LSA) of the retinal image. The examples given demonstrate that methods according to the invention are applicable for different k values of the cornea and the importance of considering pupil size and how consideration of k values for both anterior and posterior corneal surfaces effect the predictability of the methods.

Example 1

Demonstration of the Ray Tracing Technique for the Focusing Ray

In this and the following examples, a ray tracing procedure is used in determining various lens parameters such as, for example, IOL optic power and LHP. The ray tracing procedure utilized is in the form of a Microsoft Excel spreadsheet; however, any ray tracing program or routine may, in general, be utilized in various embodiments of the invention. In the ray tracing discussed here, a meridional ray impinges on a surface and follows a straight line, as expressed by $$y = y_o + ut \quad (4)$$

where $y_o$ is the radial height at the origin, u the angle (in radians) between the ray and the optical axis and t the distance, along and parallel with the optical axis, between the origin and the intersection with the surface.

The condition for intersection is that the radial height y at the surface and of the ray is the same. The calculation can be set up in an Excel spreadsheet and the Goal Seek (or Solver) utility can be used to find the value for t for which there is zero difference between the heights of the surface and of the ray. In this examples, the additional polynomial terms ($a_4 y^4$, $a_6 y^6$) are set equal to zero for simplicity, but the method is valid for non-zero values also.

The slope of the surface at the point of intersection is found by numeric differentiation. From the slope, the angle of the normal is found, and Snell's law of refraction is applied to find the angle of the refracted beam. The intersection of the refracted beam with next surface is sought as before, the slope at the point of intersection is found as before, Snell's law of refraction is again applied to find the angle of the beam leaving this surface, etc. until after refraction at the last surface the intersection between that beam and the optical axis (focus) is sought. This calculation can be set up as a macro program to perform these calculations.

A ray traced at $1/\sqrt{2} \approx 0.7$ of the height of the entrance pupil height is an average ray in the sense that it divides the pupil into two surfaces of equal area, one outer annular ring and a central circle. It is here termed the focusing ray and its intersection with the optical axis is adopted as one definition of best focus.

An alternative definition of best focus is the midpoint between a marginal ray (i.e. a ray entering at the margin of the pupil) and a paraxial ray (i.e. entering infinitesimally close to the optical axis at the pupil). The distance between the foci of the marginal and paraxial rays, the longitudinal spherical aberration (LSA) is a simple metric for optical quality of the image formed at the photoreceptor layer of the retina. The sign convention is here taken that if the paraxial ray focuses posterior to the marginal ray, the spherical aberration is termed positive. Conversely if the paraxial ray focuses anterior to the marginal ray, the spherical aberration is negative. The best image quality is when LSA is zero. The smaller the absolute value of LSA, the better the image quality.

The entrance pupil (on the first spectacle lens surface) is 5 mm in this example.

| A. CORNEA | | |
| --- | --- | --- |
| Surface | Apex radius (mm) | k |
| anterior | 7.7 | 0.82 |
| posterior | 6.8 | 0.66 |

| B. LENS | | |
| --- | --- | --- |
| Surface | Apex radius (mm) | k |
| anterior | 12.154 | −5 |
| posterior | −12.154 | −5 |

Coefficients $a_4$, $a_6$, etc. are all set equal to zero in this example.

| C. AXIAL DISTANCES | | | | | | | |
| --- | --- | --- | --- | --- | --- | --- | --- |
| Object distance | Spectacle lens thickness | Vertex distance | Corneal thickness | Anterior chamber depth | Intraocular lens thickness | Axial length | Transf. const. |
| 6 m | 2 mm | 12 mm | 0.5 mm | 4.9 mm | 1.13 mm | 23.77 mm | 0.23 mm |

Anterior chamber depth is defined here and in subsequent examples as the distance from the anterior apex of the cornea to the anterior apex of the lens (whether the natural lens or an IOL). The transformation constant, here assumed to be 0.23, transforms the measured axial length to the human population average (HPA) scale.

| D. REFRACTIVE INDICES | | | | | |
| --- | --- | --- | --- | --- | --- |
| Air | Spectacle lens | Cornea | Aqueous | Intraocular lens | Vitreous |
| 1 | 1.5 | 1.376 | 1.336 | 1.458 | 1.336 |

The macro program "Sub trace( )" is run to determine the ray path with the given input, followed by "Sub spectacle( )" to find the spectacle power giving zero ray height at the retina, i.e. the power to focus the image on the photoreceptor layer of the retina. Because changing the spectacle power changes the ray incidence on the cornea, "Sub trace( )" is run again followed by "Sub spectacle( )". Repeating this sequence a few times results in sufficient accuracy in the final result.

Figure 6:
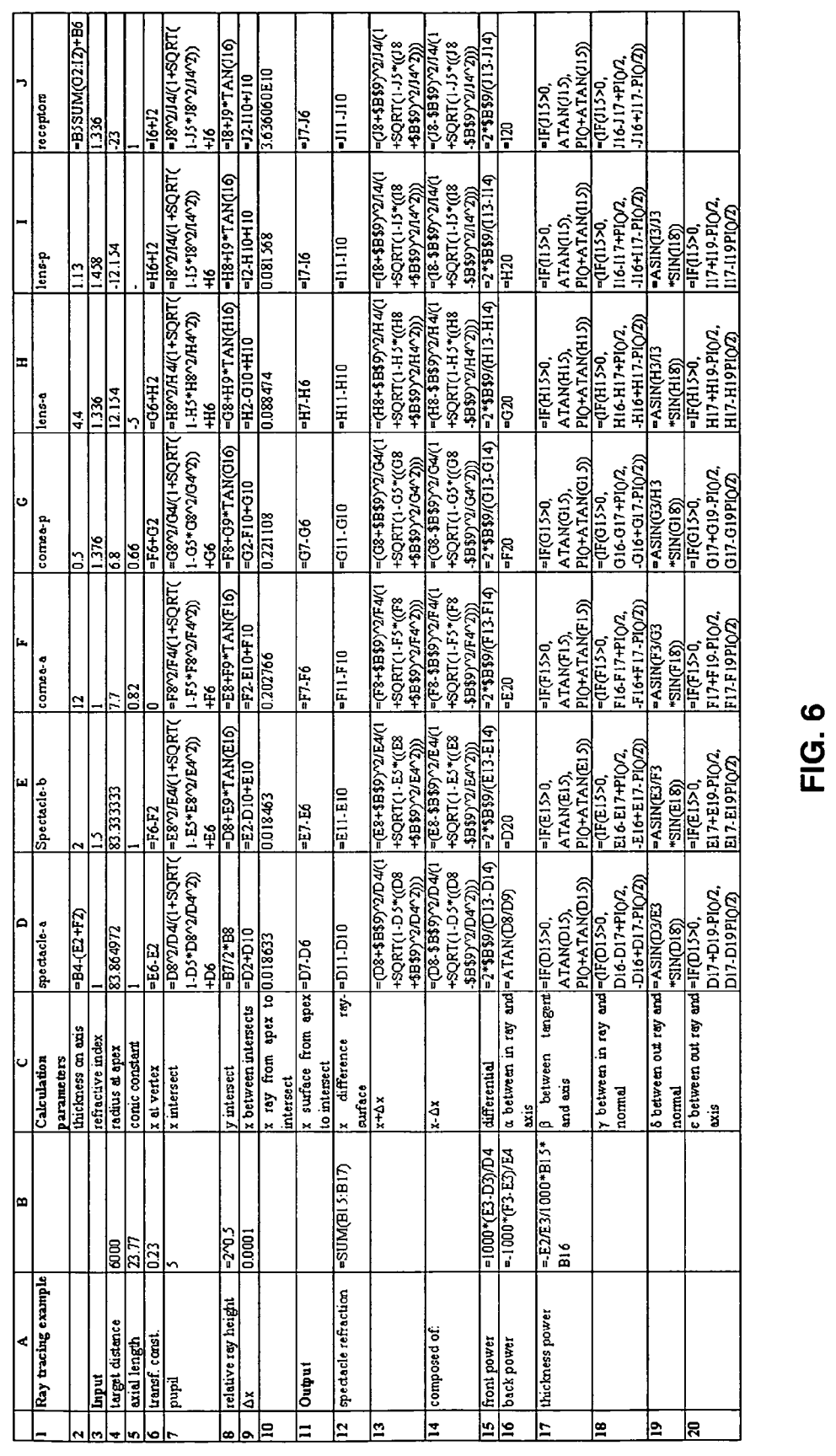

FIG. 6 illustrates the formulas programmed into each cell of the Excel spreadsheet used to provide the ray tracing program, while FIG. 7 illustrates the numerical result of the calculation in each cell. The Sub trace( ) and Sub spectacle( ) routines used in the spreadsheet model are as follows:

```
Sub trace( )
    Range("D12").GoalSeek Goal:=0, ChangingCell:=Range("D10")
    Range("E12").GoalSeek Goal:=0, ChangingCell:=Range("E10")
    Range("F12").GoalSeek Goal:=0, ChangingCell:=Range("F10")
    Range("G12").GoalSeek Goal:=0, ChangingCell:=Range("G10")
    Range("H12").GoalSeek Goal:=0, ChangingCell:=Range("H10")
    Range("I12").GoalSeek Goal:=0, ChangingCell:=Range("I10")
    Range("J12").GoalSeek Goal:=0, ChangingCell:=Range("J10")
End Sub
Sub spectacle( )
    Range("J8").GoalSeek Goal:=0, ChangingCell:=Range("D4")
End Sub
```

Figure 8:
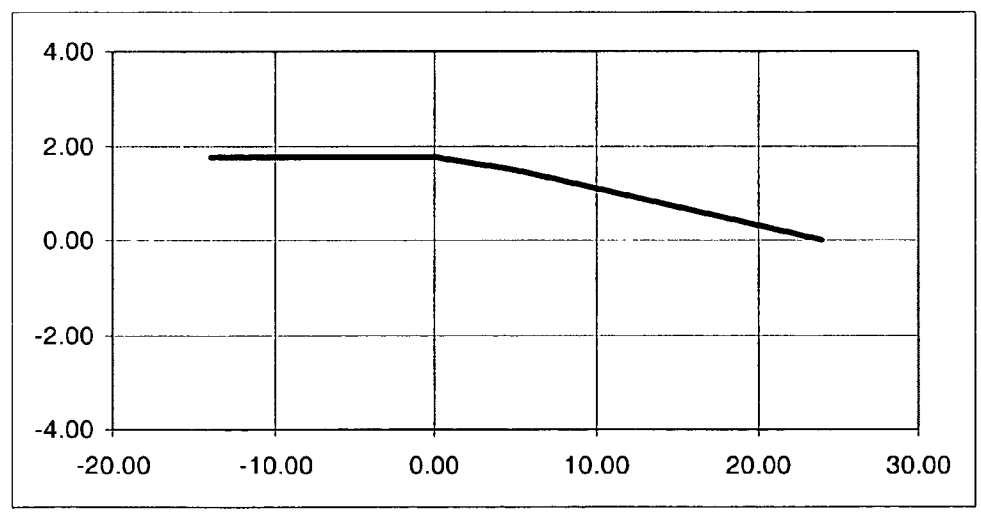
FIG. 8 is a ray trace of the numerical results presented in FIG. 7.

In the example, the spectacle power becomes +0.01D. FIG. 8.

Example 2

Selecting Power of a Spherical IOL

The entrance pupil (on the first spectacle lens surface) is 5 mm in this example.

E. CORNEA

| Surface | Apex radius (mm) | k |
|---|---|---|
| anterior | 7.87 | 0.82 |
| posterior | 6.40 | 0.66 |

The radii apply at the center of the cornea. Corneal radius determined with a keratometer applies at a circle of about 3 mm diameter. With the k-values given, 7.90 mm and 6.42 mm, respectively, would have been measured.

F. INTRAOCULAR LENSES

| G. Power (D) | Front radius (mm) | Back radius (mm) | Thickness (mm) | Vault height (mm) |
|---|---|---|---|---|
| 20.0 | 12.154 | −12.154 | 1.10 | 0.03 |
| 20.5 | 11.856 | −11.856 | 1.11 | 0.03 |
| 21.0 | 11.572 | −11.572 | 1.12 | 0.02 |

Vault height is the distance from LHP to the anterior surface of the lens (positive if the lens surface is posterior to LHP).

H. AXIAL DISTANCES

| Object distance | Spectacle lens thickness | Vertex distance | Corneal thickness | LHP | Axial length |
|---|---|---|---|---|---|
| 6 m | 2 mm | 12 mm | 0.574 mm | 4.36 mm | 23.92 mm |

LHP was calculated by the formula $$LHP = 2.486 + 0.2174 \times (AL + \Delta AL) - 0.4213 \times CR$$

where CR is the measured corneal radius (7.90 mm), AL is the measured axial length (23.69 mm) and $\Delta AL$ is the transformation constant, here assumed to be 0.23 mm. $(AL+\Delta AL)$ is the axial length transformed to the human population average (HPA) scale, which is the value given in the table. The anterior chamber depth is LHP plus the vault height for the specific IOL chosen.

I. REFRACTIVE INDICES

| Air | Spectacle lens | Cornea | Aqueous | Intraocular lens | Vitreous |
|---|---|---|---|---|---|
| 1 | 1.5 | 1.376 | 1.336 | 1.458 | 1.336 |

RESULTS

| IOL (D) | Spectacle (D) |
|---|---|
| 20.0 | +0.40 |
| 20.5 | +0.03 |
| 21.0 | −0.37 |

A surgeon would probably choose to implant the 21.0D lens. Slight myopia is often preferred.

Using the midpoint between marginal and paraxial ray foci as focusing criterion the following results are obtained.

RESULTS

| IOL (D) | Spectacle (D) |
|---|---|
| 20.0 | +0.39 |
| 20.5 | +0.01 |
| 21.0 | −0.38 |

These results are for all practical purpose equal to those obtained with the focusing ray as focusing criterion. The axial defocus of the marginal and paraxial rays in relation to the focusing rays are given in the following table.

DEFOCUS IN RELATION TO FOCUSING RAY

| IOL (D) | Marginal ray | Paraxial ray |
|---|---|---|
| 20.0 | −0.267 | +0.259 |
| 20.5 | −0.278 | +0.268 |
| 21.0 | −0.289 | +0.279 |

The marginal ray thus focuses anterior and the paraxial ray posterior to the focusing ray, indicating that the optical system has overall positive spherical aberration. The near symmetry in relation to the focusing ray is another indication of the agreement between the two focusing criteria in this example.

Example 3

Selecting Power of an Aspherical IOL

A generalized aspheric surface may be characterized using Equation (1), discussed in greater detail above herein. The entrance pupil (on the first spectacle lens surface) is 5 mm in this example.

| J. CORNEA | | |
|---|---|---|
| Surface | Apex radius (mm) | k |
| anterior | 7.87 | 0.82 |
| posterior | 6.40 | 0.66 |

The radii apply at the center of the cornea. Corneal radius determined with a keratometer applies at a circle of about 3 mm diameter. With the k-values given, 7.90 mm and 6.42 mm, respectively, would have been measured.

| K. INTRAOCULAR LENSES | | | | | |
|---|---|---|---|---|---|
| | Anterior surface | | Posterior surface | | Vault |
| Power (D) | Radius (mm) | k | Radius (mm) | k | Thickness (mm) | height (mm) |
| 20.0 | 12.154 | −7 | −12.154 | −7 | 1.13 | 0.01 |
| 20.5 | 11.856 | −7 | −11.856 | −7 | 1.13 | 0.00 |
| 21.0 | 11.572 | | −11.572 | | 1.14 | 0.00 |
| 21.5 | 11.301 | | −11.301 | | 1.15 | −0.01 |
| 22.0 | 11.043 | | −11.043 | | 1.16 | −0.01 |

Vault height is the distance from LHP to the anterior surface of the lens.

| L. AXIAL DISTANCES | | | | | |
|---|---|---|---|---|---|
| Object distance | Spectacle lens thickness | Vertex distance | Corneal thickness | LHP | Axial length |
| 6 m | 2 mm | 12 mm | 0.574 mm | 4.36 mm | 23.92 mm |

LHP was calculated by the formula, $$LHP = 2.486 + 0.2174 \times (AL + \Delta AL) - 0.4213 \times CR,$$

where CR is the measured corneal radius (7.90 mm), AL is the measured axial length (23.69 mm) and $\Delta AL$ is the transformation constant, here assumed to be 0.23 mm. $(AL+\Delta AL)$ is the axial length transformed to the human population average (HPA) scale, which is the value given in the table. The anterior chamber depth is LHP plus the vault height for the specific IOL chosen.

| M. REFRACTIVE INDICES | | | | | |
|---|---|---|---|---|---|
| Air | Spectacle lens | Cornea | Aqueous | Intraocular lens | Vitreous |
| 1 | 1.5 | 1.376 | 1.336 | 1.458 | 1.336 |

| RESULTS | |
|---|---|
| IOL (D) | Spectacle (D) |
| 20.0 | +1.19 |
| 20.5 | +0.87 |
| 21.0 | +0.57 |
| 21.5 | +0.26 |
| 22.0 | −0.04 |

Using the midpoint between marginal and paraxial ray foci as focusing criterion, the expected spectacle refraction is −0.11D with the 22.0D IOL. The focus of the marginal ray is +0.067 mm in relation to the focusing ray, i.e. focuses posterior to the focusing ray. The focus of the paraxial ray is −0.118 mm in relation to the focusing ray, i.e. focuses anterior to the focusing ray. This system thus exhibits negative spherical aberration, reversing the focusing order of the rays.

Example 4

Demonstrating the Influence of k-Value

The entrance pupil (on the first spectacle lens surface) is 5 mm in this example.

The average k-value in the human population is 0.82, with a standard deviation of 0.18 (Dubbelman, M., Weeber, H. A., van der Heijde, G. L. and Völker-Dieben, H. J. Radius and asphericity of the posterior corneal surface determined by corrected Scheimpflug photography. Acta Ophthalmol Scand 2002; 80: 379-383).

For illustration a 20.5D spherical lens and a 21.5D aspherical lens with the following designs are chosen.

| N. INTRAOCULAR LENSES | | | | | | | | | |
|---|---|---|---|---|---|---|---|---|---|
| | Anterior surface | | | | Posterior surface | | | | Vault |
| Power (D) | Radius (mm) | k | $a_4$ (mm$^{-4}$) | $a_6$ (mm$^{-6}$) | Radius (mm) | k | $a_4$ (mm$^{-4}$) | $a_6$ (mm$^{-6}$) | Thickness (mm) | height (mm) |
| 20.5 spherical | 11.856 | 1 | 0 | 0 | −11.856 | 1 | 0 | 0 | 1.11 | 0.03 |
| 21.5 aspherical | 11.301 | −4 | $-1 \cdot 10^{-4}$ | $1 \cdot 10^{-6}$ | −11.301 | −4 | 0 | 0 | 1.15 | −0.01 |

Assume that the surgeon has come to these lens powers with a calculation method that does not take corneal asphericity into account. Which influence will variation of up to 3 standard deviations of corneal asphericity have on postoperative refraction?

The keratometrically (at 3 mm diameter) measured anterior corneal radius is assumed to be 7.90 mm. The posterior radius is unknown, but is as in previous examples assumed to be 6.42 mm (at 3 mm diameter) and have a k-value of 0.66. The shape of the posterior surface is further assumed to be independent of that of the anterior surface and remain unchanged when the k-value of the anterior surface is varied.

O. ANTERIOR CORNEAL SURFACE

| ±SD | P. Surface characteristics | | Q. Apex radius (mm) |
|---|---|---|---|
| | k | type | |
| −3 | 0.28 | prolate | 7.79 |
| −2 | 0.46 | prolate | 7.82 |
| −1 | 0.64 | prolate | 7.84 |
| ±0 | 0.82 | prolate | 7.87 |
| +1 | 1.00 | sphere | 7.90 |
| +2 | 1.18 | oblate | 7.92 |
| +3 | 1.36 | oblate | 7.95 |

R. AXIAL DISTANCES

| Object distance | Spectacle lens thickness | Vertex distance | Corneal thickness | LHP | Axial length (transformed) |
|---|---|---|---|---|---|
| 6 m | 2 mm | 12 mm | 0.574 mm | 4.36 mm | 23.92 mm |

S. REFRACTIVE INDICES

| Air | Spectacle lens | Cornea | Aqueous | Intraocular lens | Vitreous |
|---|---|---|---|---|---|
| 1 | 1.5 | 1.376 | 1.336 | 1.458 | 1.336 |

S. REFRACTIVE INDICES

RESULTS

| | | Spectacle correction (D) with | |
|---|---|---|---|
| SD | k | Spherical IOL 20.5 D | Aspherical IOL 21.5 D |
| −3 | −0.72 | 0.21 | 0.23 |
| −2 | −0.54 | 0.15 | 0.15 |
| −1 | −0.36 | 0.09 | 0.07 |
| ±0 | −0.18 | 0.03 | −0.01 |
| +1 | 0.00 | −0.04 | −0.10 |
| +2 | 0.18 | −0.10 | −0.18 |
| +3 | 0.36 | −0.17 | −0.27 |

This example shows that the effect of neglecting corneal asphericity in IOL power calculation has effect on the postoperative refraction for spherical as well as for aspherical IOLs.

Example 5

Finding the Influence of Pupil Size

The entrance pupil is defined on the first spectacle lens surface and is varied in this example.

For this example a 20.5D spherical lens and a 21.5D aspherical lens with the following designs are chosen.

T. INTRAOCULAR LENSES

| | Anterior surface | | | | Posterior surface | | | | | Vault |
|---|---|---|---|---|---|---|---|---|---|---|
| Power (D) | Radius (mm) | k | $a_4$ (mm$^{-4}$) | $a_6$ (mm$^{-6}$) | Radius (mm) | k | $a_4$ (mm$^{-4}$) | $a_6$ (mm$^{-6}$) | Thickness (mm) | height (mm) |
| 20.5 spherical | 11.856 | 1 | 0 | 0 | −11.856 | 1 | 0 | 0 | 1.11 | 0.03 |
| 21.5 aspherical | 11.301 | 0 | $-1 \cdot 10^{-3}$ | $1 \cdot 10^{-6}$ | −11.301 | 1 | 0 | 0 | 1.15 | −0.01 |

Normally pupil size is not considered in IOL power calculation. About 4 mm is common at mesopic light conditions (dusk), but individual variations from 2 mm up to 6 mm or even wider are known. What could the consequences be for patients depending on pupil size?

The following additional parameters are assumed.

U. CORNEA

| Surface | Apex radius (mm) | k |
|---|---|---|
| anterior | 7.87 | 0.82 |
| posterior | 6.40 | 0.66 |

V. AXIAL DISTANCES

| Object distance | Spectacle lens thickness | Vertex distance | Corneal thickness | LHP | Axial length (transformed) |
|---|---|---|---|---|---|
| 6 m | 2 mm | 12 mm | 0.574 mm | 4.36 mm | 23.92 mm |

W. REFRACTIVE INDICES

| Air | Spectacle lens | Cornea | Aqueous | Intraocular lens | Vitreous |
|---|---|---|---|---|---|
| 1 | 1.5 | 1.376 | 1.336 | 1.458 | 1.336 |

X. RESULTS

| | Postoperative refraction (D) with | |
|---|---|---|
| Pupil (mm) | Spherical IOL 20.5 D | Aspherical IOL 21.5 D |
| 2 | +0.62 | +0.02 |
| 3 | +0.49 | +0.06 |
| 4 | +0.29 | +0.10 |
| 5 | +0.03 | +0.15 |
| 6 | −0.32 | +0.20 |

This example shows that the pupil size can have large effects on postoperative refraction, in particular in an eye with much spherical aberration, i.e. in the normal case an eye with a spherical IOL. The aspherical IOL in this example corrects for most of the spherical aberration of the cornea, but not all, hence there is some effect of pupil size on postoperative refraction. However, if the corneal aberrations were perfectly corrected by the IOL, there would be no effect of pupil size on postoperative refraction.

Example 6

Consequence of not Knowing the Posterior Corneal Curvature

The entrance pupil (on the first spectacle lens surface) is 5 mm in this example.

For this example a 20.5D spherical lens and a 22.0D aspherical lens with the following designs are chosen.

Y. INTRAOCULAR LENSES

| | Anterior surface | | Posterior surface | | | Vault |
|---|---|---|---|---|---|---|
| Power (D) | radius (mm) | k | radius (mm) | k | Thickness (mm) | height (mm) |
| 20.5 spherical | 11.856 | 1 | −11.856 | 1 | 1.11 | 0.03 |
| 22.0 aspherical | 11.043 | −7 | −11.043 | −7 | 1.16 | −0.01 |

Coefficients $a_4$, $a_6$, etc. are all set equal to zero in this example.

In the normal case only the anterior radius of the cornea is measured, known and used in IOL power calculation. Corneal thickness, posterior radius and posterior asphericity is generally not known. What are the consequences of making assumptions about these unknown quantities?

Assume as before that the corneal curvature (at 3 mm) measured by keratometry was found to be 7.90 mm.

Z. CORNEAL CASES

| | Anterior surface | | Posterior surface | | Thickness (mm) | Ratio of radii (posterior/anterior) |
|---|---|---|---|---|---|---|
| | Apex radius (mm) | k | Apex radius (mm) | k | | |
| Case 1 | 7.87 | 0.82 | 6.40 | 0.66 | 0.574 | 0.81 |
| Case 2 | 7.87 | 0.82 | 6.40 | 1.00 | 0.574 | 0.81 |
| Case 3 | 7.87 | 0.82 | 7.30 | 0.82 | 0.574 | 0.93 |
| Case 4 | 7.87 | 0.82 | 6.40 | 0.66 | 0.000 | 0.81 |
| Case 5 | 7.87 | 0.82 | 6.95 | 1.00 | 0.574 | 0.88 |
| Case 6 | 7.87 | 1.00 | 6.40 | 1.00 | 0.574 | 0.81 |

Case 1 is considered to have the proper values for all variables. The ratio of radii is taken from Dubbelman et al. Acta Ophthalmol Scand 2002; 80:379-383. In Case 2 the posterior surface is assumed to be spherical. In Case 3 the posterior surface is assumed to be concentric with the anterior surface and having the same asphericity, which leads to the ratio of radii given. In Case 4 the corneal thickness is neglected. In Case 5 the ratio of radii is assumed to follow the classic Gullstrand model, i.e. 6.8/7.7. In Case 6 both surfaces are assumed spherical.

The following additional parameters are assumed.

AA. AXIAL DISTANCES

| Object distance | Spectacle lens thickness | Vertex distance | Corneal thickness | Axial length (transformed) |
|---|---|---|---|---|
| 6 m | 2 mm | 12 mm | 0.574 mm | 23.92 mm |

BB. REFRACTIVE INDICES

| Air | Spectacle lens | Cornea | Aqueous | Intraocular lens | Vitreous |
|---|---|---|---|---|---|
| 1 | 1.5 | 1.376 | 1.336 | 1.458 | 1.336 |

CC. RESULTS

| | Postoperative refraction (D) with | |
|---|---|---|
| | Spherical IOL 20.5 D | Aspherical IOL 22.0 D |
| Case 1 | +0.03 | −0.04 |
| Case 2 | +0.11 | +0.04 |
| Case 3 | −0.74 | −0.78 |
| Case 4 | +0.25 | +0.18 |

-continued

CC. RESULTS

| | Postoperative refraction (D) with | |
|---|---|---|
| | Spherical IOL 20.5 D | Aspherical IOL 22.0 D |
| Case 5 | −0.42 | −0.47 |
| Case 6 | +0.04 | +0.03 |

Whether the IOL is spherical or aspherical this example shows that the posterior corneal radius, i.e. the assumed ratio of radii, has the largest influence (Cases 3 and 5). Putting corneal thickness equal to zero (Case 4) causes less than a quarter of dioptre increase in refraction. Neglecting posterior corneal asphericity (Case 2) has little influence, and simultaneously disregarding asphericity of both surfaces (Case 6) has close to negligible influence. This result is coincidental though. Other initial asphericities would give different results as can be inferred from Example 4.

Example 7

Alternative Calculations Using Optical Design Programs

The entrance pupil (on the first spectacle lens surface) is 5 mm in this example.

For illustration a 20.5D spherical lens and a 22.0D aspherical lens with the following designs are chosen.

DD. INTRAOCULAR LENSES

| | Anterior surface | | Posterior surface | | |
|---|---|---|---|---|---|
| Power (D) | radius (mm) | k | radius (mm) | k | Thickness (mm) |
| 20.5 spherical | 11.856 | 1 | −11.856 | 1 | 1.11 |
| 22.0 aspherical | 11.043 | −7 | −11.043 | −7 | 1.16 |

Using the optical design software OSLO alternative focusing criteria were evaluated

- Minimum on-axis spot size
- Minimum RMS OPD on axis
- Maximum MTF at 20 cycles/mm
- Maximum MTF at 50 cycles/mm Calculations are monochromatic assuming the following refractive indices.

EE. REFRACTIVE INDICES

| Air | Spectacle lens | Cornea | Aqueous | Intraocular lens | Vitreous |
|---|---|---|---|---|---|
| 1 | 1.5 | 1.376 | 1.336 | 1.458 | 1.336 |

The keratometrically (at 3 mm diameter) measured anterior corneal radius is assumed to be 7.90 mm. The posterior radius is unknown, but is as in previous examples assumed to be 6.42 mm (at 3 mm diameter) and have a k-value of 0.66. The apex radii are slightly steeper due to the asphericity.

FF. CORNEA

| Surface | Apex radius (mm) | k |
|---|---|---|
| anterior | 7.87 | 0.82 |
| posterior | 6.40 | 0.66 |

Other parameters are as follows.

GG. AXIAL DISTANCES

| IOL type | Object distance (m) | Spectacle lens thickness (mm) | Vertex distance (mm) | Corneal thickness (mm) | Aqueous thickness (mm) | Vitreous thickness (mm) |
|---|---|---|---|---|---|---|
| Spherical | 6 | 2 | 12 | 0.574 | 3.811 | 18.425 |
| Aspherical | | | | | 3.771 | 18.415 |

Vitreous thickness includes an assumed 0.25 mm retinal thickness.

RESULTS

| | Spectacle power (D) with | |
|---|---|---|
| FOCUSING CRITERION | Spherical IOL of 20.5 D power | Aspherical IOL of 22.0 D power |
| Minimum spot size | −0.27 | +0.03 |
| Minimum RMS OPD | −0.01 | −0.05 |
| Max MTF @ 20 c/mm | −0.16 | +0.01 |
| Max MTF @ 50 c/mm | +0.26 | −0.01 |
| Focusing ray | +0.03 | −0.04 |

It can be seen that the Minimum RMS OPD criterion, which is a commonly accepted definition of best focus, agrees well with the focusing ray for both the spherical and the aspherical IOLs. The considerable amount of spherical aberration in case of the spherical IOL causes the various focusing criteria to disagree.

The through-focus MTF plots (output by the OSLO program) at 20 and 50 cyc/mm used to determine maximum MTF are shown in FIGS. 9A-9D. The horizontal line at the top is the diffraction limited MTF of the system at the spatial frequency given.

Example 8

Correcting Extreme Corneal Aberrations by Adjusting the Shape of the IOL

The entrance pupil (on the first spectacle lens surface) is 4 mm in this example.

The k-value can vary considerably outside the normal range (see Example 4) in persons who have undergone corneal refractive surgery. Correction of myopia tends to make the corneal spherical aberration more positive (towards oblate), while correction of hyperopia tends to make the corneal spherical aberration more negative (towards hyperopic) (Buehren et al., Scientific poster 144, AAO 2004, New Orleans).

Consider two eyes, one originally −5D axially myopic and the other +5D axially hyperopic. They thus differ in axial length and proportionally in anterior chamber depth. However, their corneas and lenses are originally assumed to be identical. Their refractive state is characterized by the spectacle spherical equivalent (SE) and longitudinal spherical aberration (LSA). The anterior chamber depth was estimated from clinical data for eyes of corresponding lengths.

For this example the following refractive indices are assumed.

| HH. REFRACTIVE INDICES | | | | | |
|---|---|---|---|---|---|
| Air | Spectacle lens | Cornea | Aqueous, vitreous | Crystalline lens | Intraocular lens |
| 1 | 1.5 | 1.376 | 1.336 | 1.4274 | 1.458 |

The eyes can now be summarized as follows.

| 1. ORIGINAL STATUS OF THE EYES | | | | | | | | | | | | | |
|---|---|---|---|---|---|---|---|---|---|---|---|---|---|
| Refractive state | | | Cornea | | | | | Crystalline lens | | | | | |
| | | | Anterior | | Posterior | | | Anterior | | Posterior | | | Ocular distances |
| | | | Apex | | Apex | | Thick- | Apex | | Apex | | Thick- | |
| Original ametropia | SE (D) | LSA (mm) | radius (mm) | k | radius (mm) | k | ness (mm) | radius (mm) | k | radius (mm) | k | ness (mm) | AL (mm) ACD (mm) LHP (mm) |
| Myopic | −5.0 | 0.084 | 7.870 | 0.82 | 6.400 | 0.66 | 0.574 | 10.670 | −3 | −5.848 | −2 | 3.76 | 25.43 3.47 4.74 |
| Hyperopic | +5.0 | 0.023 | 7.870 | 0.82 | 6.400 | 0.66 | 0.574 | 10.670 | −3 | −5.848 | −2 | 3.76 | 21.62 2.96 3.91 |

LHP was calculated from the formula $$LHP = 2.486 + 0.2174 \times (AL + \Delta AL) - 0.4213 \times CR$$

in which the transformation constant $\Delta AL$ was set to 0.25 mm and the corneal radius at 3 mm CR is 7.896 mm with the apex radius and k-value as given in the table.

Assume that these eyes undergo corneal refractive surgery to make them emmetropic. Besides correcting the spherical equivalent the myopic eye is assumed to become one unit of k-value towards oblate, and the hyperopic eye is assumed to become one unit of k-value towards hyperopic. The myopic correction further results in decrease of the central thickness of the cornea amounting to 0.060 mm, while the hyperopic correction does not cause any change of the central thickness of the cornea. The decrease in corneal thickness causes a corresponding decrease in AL, ACD and LHP in the myopic case. The following situation ensues.

| 2. STATUS OF THE EYES AFTER CORNEAL REFRACTIVE SURGERY | | | | | | | | | | | | | |
|---|---|---|---|---|---|---|---|---|---|---|---|---|---|
| Refractive state | | | Cornea | | | | | Crystalline lens | | | | | |
| | | | Apex | | Apex | | Thick- | Apex | | Apex | | Thick- | Ocular distances |
| Original ametropia | SE (D) | LSA (mm) | radius (mm) | k | radius (mm) | k | ness (mm) | radius (mm) | k | radius (mm) | k | ness (mm) | AL (mm) ACD (mm) LHP (mm) |
| Myopic | 0.00 | 0.434 | 8.794 | 1.82 | 6.400 | 0.66 | 0.514 | 10.670 | −3 | −5.848 | −2 | 3.76 | 25.37 3.41 4.68 |
| Hyperopic | 0.00 | −0.522 | 6.967 | −0.18 | 6.400 | 0.66 | 0.574 | 10.670 | −3 | −5.848 | −2 | 3.76 | 21.62 2.96 3.91 |

Note that the myopic eye now has considerable positive spherical aberration (LSA) and that the surgery of the hyperopic has even reversed the sign and resulted in considerable negative spherical aberration (LSA) of the entire eye.

Assume that these eyes several years later are eligible for cataract surgery. The aim of the surgery is emmetropia (with the target at 6 m) and elimination of spherical aberration. The following lenses are designed for this purpose.

| | IOL | | | | | | | | | | |
|---|---|---|---|---|---|---|---|---|---|---|---|
| | | | Vault | Anterior surface | | | | Posterior surface | | | |
| Original ametropia | Power (D) | Thickness (mm) | height (mm) | radius (mm) | k | a4 (mm$^{-4}$) | A6 (mm$^{-6}$) | radius (mm) | k | a4 (mm$^{-4}$) | a6 (mm$^{-6}$) |
| Myopic | 23.20 | 1.19 | −0.02 | 10.468 | −5.45 | −1.00·10$^{-3}$ | −4.85·10$^{-5}$ | −10.468 | 1 | 0 | 0 |
| Hyperopic | 20.23 | 1.13 | 0.00 | 12.012 | 2.45 | 8.80·10$^{-4}$ | −1.40·10$^{-5}$ | −12.012 | 1 | 0 | 0 |

The situation is now characterized as follows.

| 3. STATUS OF THE EYES AFTER CATARACT SURGERY | | | | | | | | | | |
|---|---|---|---|---|---|---|---|---|---|---|
| | | | Cornea | | | | | | | |
| | | | Anterior | | Posterior | | | | | |
| Refractive state | | | Apex | | Apex | | Thick- | Ocular distances | | |
| Original ametropia | SE (D) | LSA (mm) | radius (mm) | k | radius (mm) | k | ness (mm) | AL (mm) | ACD (mm) | LHP (mm) |
| Myopic | 0.00 | 0.00 | 8.794 | 1.82 | 6.400 | 0.66 | 0.514 | 25.37 | 4.66 | 4.68 |
| Hyperopic | 0.00 | 0.00 | 6.967 | −0.18 | 6.400 | 0.66 | 0.574 | 21.62 | 3.91 | 3.91 |

This example shows that intraocular lenses can be designed to correct rotationally symmetrical aberrations, i.e. sphere and spherical aberration, for eyes having extreme corneal spherical aberration.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A computer system for selecting, from a plurality of IOLs, an IOL for placement into the eye of a subject, comprising:
    a processor; and
    a computer readable memory coupled to the processor, the memory having stored therein:
        an array of ordered values, including:
            one or more ocular dimensions of the subject;
            a desired refractive outcome;
            for each IOL of the plurality of IOLs, a power and an aspheric constant, the power of each IOL being different;
            parameters of an eye model based on one or more characteristics of at least one eye; and
        a ray tracing algorithm, wherein the processor is configured to perform one or more calculations to determine a predicted refractive outcome based on the eye model and the ray tracing algorithm; and
        sequences of instructions which, when executed by the processor, cause the processor to select, from the plurality of IOLs, an IOL for implantation into the eye of the subject, wherein the selection of the IOL is based at least in part on the anterior and/or posterior corneal curvature and the pupil size of the eye of the subject to receive the IOL; wherein the sequences of instructions includes:
        performing a calculation for the predicted refractive outcome based on the eye model and the ray tracing algorithm from which the longitudinal spherical aberration (LSA) is calculated as the distance between foci of a marginal ray and a paraxial ray; and
        determining if the LSA is sufficiently low and if not selecting another lens with a different power, a different aspheric constant, and/or a different lens plane.

2. The computer system of claim 1 wherein the characteristic of the eye is one or more of an axial length of the eye, a pupil size of the eye, and crystalline lens thickness of the eye.

3. The computer system of claim 1 wherein the desired refractive outcome is providing a subject with distant vision, providing a subject with near vision, or providing a subject with both distant vision and near vision.

4. The computer system of claim 1 wherein each IOL is characterized by a conicoid surface of revolution having an aspheric constant k that is between zero and one.

5. The computer system of claim 1 wherein the parameters of the eye model include at least one cornea of the at least one eye, the at least one cornea having an aspheric representation of an anterior corneal surface, wherein a shape of the corneal surface is derived from corneal topography.

6. The computer system of claim 1 wherein the computer readable memory has stored therein an aspheric representation of a model IOL.

7. The computer system of claim 6 wherein the aspheric representation includes an aberration of the model IOL.

8. The computer system of claim 6 wherein the aspheric representation includes an aspheric representation of a surface of the model IOL.

9. The computer system of claim 6 wherein aspheric representation of the model IOL includes at least one surface described according to the formula:

$$x = \frac{\left(\frac{1}{R}\right)y^2}{1+\sqrt{1-k\left(\frac{1}{R}\right)^2 y^2}} + a_4 y^4 + a_6 y^6 + \ldots$$

wherein R is the radius of curvature at the apex, k is the conic constant, y is the radial distance from the optical axis and x is the sag in the direction of light propagation.

10. The computer system of claim 6 wherein the polynomial terms $a_4, a_6 \ldots$ are zero.

11. The computer system of claim 1 wherein the computer system is a phacoemulsification system.

12. The computer system of claim 1 wherein the computer system is an instrument for obtaining measurements of an eye.

13. The computer system of claim 1 wherein the computer system is a handheld device.

14. The computer system of claim 1 wherein the array of ordered values includes an eye model.

15. The computer system of claim 1 wherein the eye model includes the lens haptic plane, the location of the lens haptic plane being obtained with a prediction algorithm that includes input values of measured axial eye length and a measured corneal radius or a corneal power (K).

16. The computer system of claim 15 wherein the prediction algorithm is of the type:

$$LHP = a + b \times AL + c \times ACD + d \times LT + e \times CR +$$
$$f \times AL^2 + g \times ACD^2 + h \times LT^2 + i \times CR^2 +$$
$$j \times AL \times ACD + k \times AL \times LT + l \times AL \times CR +$$
$$m \times ACD \times LT + n \times ACD \times CR + o \times LT \times CR$$

wherein AL is the axial eye length, CR the corneal radius, or alternatively corneal power (K), ACD the anterior chamber depth, and LT the crystalline lens thickness.

* * * * *